US012670139B1

(12) United States Patent
Mason et al.

(10) Patent No.: US 12,670,139 B1
(45) Date of Patent: Jun. 30, 2026

(54) DETERMINING DATA LINKS BASED ON RECONSTRUCTING DATA IDENTIFIERS

(71) Applicant: Ancestry.com DNA, LLC, Lehi, UT (US)

(72) Inventors: Clinton C. Mason, Lehi, UT (US); Yong Wang, San Mateo, CA (US)

(73) Assignee: Ancestry.com DNA, LLC, Lehi, UT (US)

( * ) Notice: Subject to any disclaimer, the term of this patent is extended or adjusted under 35 U.S.C. 154(b) by 0 days.

(21) Appl. No.: 19/090,081

(22) Filed: Mar. 25, 2025

(51) Int. Cl.
*G06F 16/22* (2019.01)
*G06F 16/25* (2019.01)
*G16B 40/20* (2019.01)

(52) U.S. Cl.
CPC ........ *G06F 16/2228* (2019.01); *G06F 16/252* (2019.01); *G16B 40/20* (2019.02)

(58) Field of Classification Search
CPC .... G06F 16/2228; G06F 16/252; G16B 40/20
See application file for complete search history.

(56) References Cited

U.S. PATENT DOCUMENTS

| | | | | |
|---|---|---|---|---|
| 11,482,306 | B2 * | 10/2022 | Song | G16B 20/00 |
| 11,514,627 | B2 * | 11/2022 | Jewett | G06T 11/26 |
| 2003/0172065 | A1 * | 9/2003 | Sorenson | G16B 10/00 |
| 2017/0011042 | A1 * | 1/2017 | Kermany | G16B 50/30 |
| 2017/0329866 | A1 * | 11/2017 | Macpherson | G16H 10/60 |

* cited by examiner

*Primary Examiner* — Kris E Mackes
(74) *Attorney, Agent, or Firm* — Keller Preece PLLC

(57) ABSTRACT

The present disclosure is directed toward systems, methods, and non-transitory computer-readable media that more accurately determine matches between data identifiers based on data identifier reconstruction. For example, the disclosed systems determine a cognate dataset which can include a data identifier associated with a source individual along with data identifiers of individuals related to the source individual. From the cognate dataset, the disclosed systems can reconstruct a data identifier for a precursor entity of the source individual. In some embodiments, the disclosed systems can determine a data link between a target individual and the source individual by determining a data link between the reconstructed data identifier and the target individual and by modifying the data link based on a relationship between the precursor entity and the source individual.

20 Claims, 13 Drawing Sheets

900

Generating A Reconstructed Data Identifier For A Precursor Entity _902_

Generating A Precursor Data Match _904_

Determining A Source Match Relationship _906_

1100

DETERMINING DATA LINKS BASED ON RECONSTRUCTING DATA IDENTIFIERS

BACKGROUND

In the field of genealogical data analysis, existing systems can provide some opportunities to assess genealogical data and connect individuals in genealogical data structures. For instance, existing systems often rely on manual genealogical data tree stitching, enabling users to manually build, compare, and modify genealogical data trees. In other cases, existing systems may use cumulative centimorgan (cM) thresholds or identical-by-descent (IBD) segment matching to make inferences as to a genealogical relationship between a source individual and a target individual. For example, some existing systems use cM thresholds to infer a genealogical relationship based on total shared cMs between the source individual and the target individual, using predefined thresholds. As another example, existing systems may use IBD segment matching to identify overlapping IBD segments in genetic data associated with the source individual and the target individual to infer a genealogical relationship between the two. Nevertheless, existing systems exhibit a number of deficiencies or drawbacks, particularly in relation to accuracy, speed, and capacity to analyze, modify, and/or compare large amounts of genealogical and genetic data.

As just suggested, some existing systems are inaccurate. For instance, existing systems that rely on manual genealogical data tree stitching depend heavily on user input and manual record comparison which is not only slow but also prone to error, redundancy, and inaccuracy. Further, as the genealogical data trees grow and interlink, accurately managing the large amounts of data manually becomes infeasible without more integrated computer systems. In addition, these systems are often limited to inferring genealogical relationships based entirely (or nearly entirely) on known genealogical records and user submitted data that may contain inaccuracies or incomplete information. Relying on such flawed foundational data leads to inaccurate construction of comprehensive genealogical data trees.

Existing systems that use cM thresholds or IBD segment matching are likewise inaccurate or at least incomplete. Indeed, some systems rely primarily or exclusively on data associated only with individuals directly involved in a match comparison which may or may not provide a complete picture of genetic data to compare. Because such genetic data is often missing or incomplete, existing systems often make inaccurate inferences of relationships between individuals.

In addition to their inaccuracies, many existing systems are too slow to analyze, modify, and/or compare large amounts (e.g., terabytes or more) of genealogical and genetic data. For example, because of their reliance on manual (e.g., user-interaction-based) genealogical data tree stitching, many existing systems require excessive amounts of time and computational resources to determine genealogical relationships and create genealogical data trees. Not only are such systems too slow to process large amounts of genealogical records to form accurate genealogical data trees, but such existing systems are likewise too slow to process corresponding genetic data. Indeed, it is impractical if not impossible for existing user-interaction-based systems to analyze and compare terabytes (or more) of genetic data with terabytes (or more) of genealogical records to identify correspondences or relationships.

These along with additional problems and issues exist with regard to existing systems.

SUMMARY

This disclosure describes one or more embodiments of systems, methods, and non-transitory computer-readable storage media that provide benefits and/or solve one or more of the foregoing and other problems in the art. In particular, the disclosed systems introduce a unique approach to more accurately determining matches between data identifiers based on data identifier reconstruction. For example, the disclosed systems determine a cognate dataset which can include a data identifier associated with a source individual along with data identifiers of individuals related to the source individual. From the cognate dataset, the disclosed systems can reconstruct a data identifier for a precursor entity of the source individual. In some embodiments, the disclosed systems can determine a data link between a target individual and the source individual by determining a data link between the reconstructed data identifier and the target individual and by modifying the data link based on a relationship between the precursor entity and the source individual.

BRIEF DESCRIPTION OF THE DRAWINGS

The detailed description provides one or more embodiments with additional specificity and detail through the accompanying drawings, as briefly described below.

DETAILED DESCRIPTION

Figure 1:
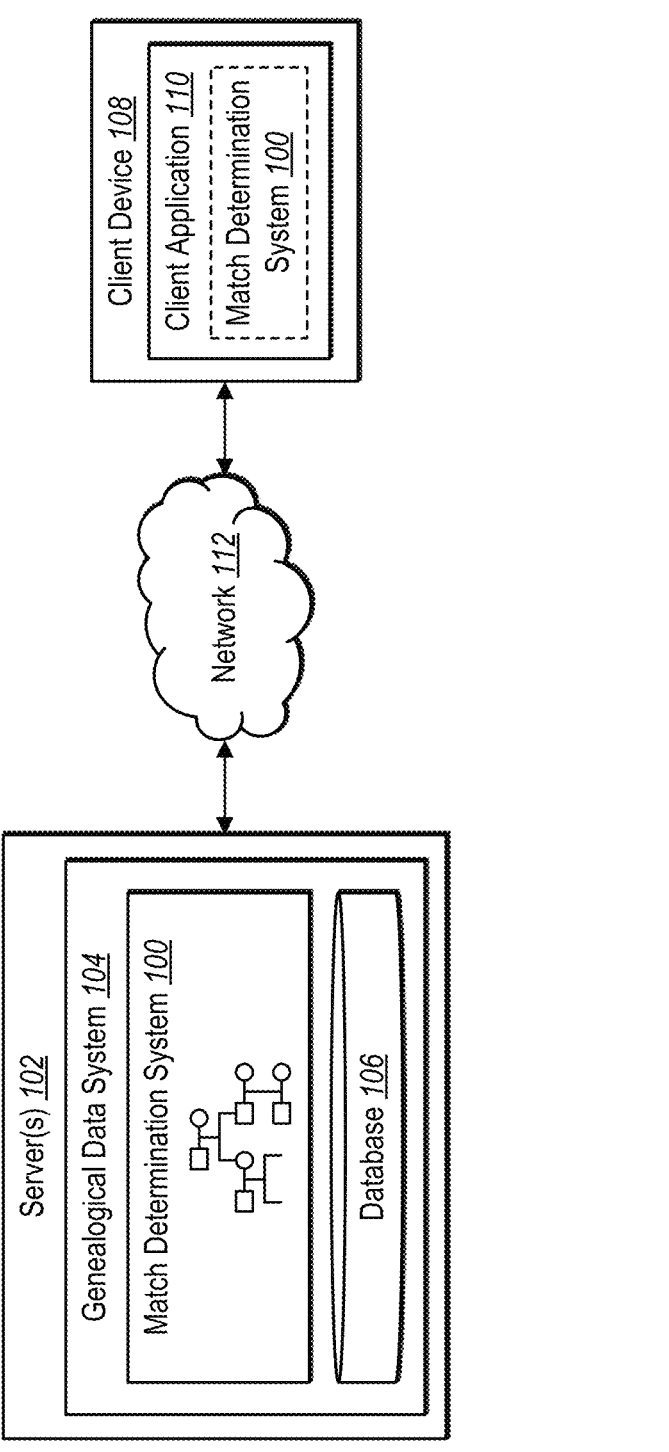
FIG. 1 illustrates a schematic diagram of an example system environment for implementing a match determination system in accordance with one or more embodiments.

This disclosure describes one or more embodiments of a match determination system 100 that can, with increased accuracy as compared to prior systems, determine a data link between a target individual and a source individual. For example, the match determination system 100 receives data identifiers (e.g., genomic or genetic data markers, such as a genome sequence or a genome segment) for each individual in a cognate dataset, which can include data identifiers for a source individual and/or one or more of his/her siblings and/or other relatives. From the cognate dataset, the match determination system 100 can reconstruct a data identifier (e.g., a reconstructed genome) for a precursor entity (e.g., an ancestor, such as a parent) of the source individual. In some embodiments, the match determination system 100 generates a data match between the precursor entity and the target individual by utilizing the reconstructed data identifier of the precursor entity. Based on the data match and further based on a relationship between the source individual and the precursor entity, the match determination system 100 can determine the data link between the target individual and the source individual.

In one or more embodiments, the match determination system 100 can provide several improvements or advantages over existing systems. For instance, the match determination system 100 can improve accuracy over existing systems. To elaborate, the match determination system 100 can more accurately determine data links (or familial relationships) between data identifiers (or individuals) by leveraging reconstructed data identifiers for precursor entities. Thus, unlike prior systems that rely on directly comparing two data identifiers (or individuals) to determine their data link, the match determination system 100 reconstructs a data identifier for a precursor entity to use in more accurately determining a data link (or a familial relationship) and/or in disambiguating potential data links (or familial relationships). Indeed, the match determination system 100 can use a reconstructed data identifier to disambiguate potential data links that indicate meiosis-level connections or links between data identifiers and/or to disambiguate potential familial relationships, such as nibling relationships (e.g., relationships between an individual and descendants of their siblings), pibling relationships (e.g., relationships between an individual and siblings of their ancestor), parental relationships, or others.

To elaborate, by utilizing a reconstructed data identifier for a precursor entity, the match determination system 100 can reconstruct a data identifier for a precursor entity. From this reconstruction, the match determination system 100 can inform or modify a genetic dataset corresponding to a source individual. For instance, by reconstructing a data identifier for a precursor entity of the source individual, the match determination system 100 can better determine heritable characteristics between the precursor entity and the source individual, thereby facilitating better disambiguation of a (most likely) data link (or familial relationship) from among the noise of potential data links (or familial relationships). Consequently, the match determination system 100 can also reduce or eliminate the impact of human error in generating genealogical data trees from large-scale datasets. Indeed, the match determination system 100 can generate, modify, or verify data links indicated within a genealogical data tree by accurately determining placement for nodes and edges according to reconstructed data identifiers, all without (or with relatively little) user input or manual record comparisons.

To elaborate on the accuracy improvement, while existing systems rely primarily or exclusively on data associated only with individuals directly involved in the comparison, the match determination system 100 can reconstruct a data identifier (e.g., a genome) for a precursor entity for more accurate, reliable predictions of data links and/or familial relationships. For example, the match determination system 100 can reconstruct a data identifier for a precursor entity from data identifiers of a cognate dataset that includes data for a source individual and/or one or more relatives (e.g., siblings) of the source individual. Indeed, in some cases, a cognate dataset includes data for a source individual while in other cases a cognate dataset does not include data for the source individual and instead includes only data for relatives of the source individual. By leveraging the cognate dataset for relationship predictions, the match determination system 100 can improve accuracy at least by identifying and mitigating errors or anomalies in genomic or genetic data, comparing haplotypes (e.g., of siblings) to identify locations of recombination breakpoints in each chromosome (e.g., each autosome) with greater precision, and/or phasing data associated with each member of the cognate dataset to more accurately generate a reconstructed data identifier as the basis for data link (relationship) prediction. Indeed, the match determination system 100 can generate more accurate data links and/or relationships using a reconstructed data identifier compared to prior systems that attempt to predict data links directly between a source individual and a target individual without using a reconstructed data identifier.

As an example, if a prior system was to rely on a data match between the source individual and the target individual, the prior system may infer that a source individual and a target individual share 631 cMs. Based on this inference, the prior system may then infer that the source individual and the target individual have an M5 meiosis-separation relationship and are first cousins once removed. By contrast, the match determination system 100 can determine that the precursor entity-via a reconstructed data identifier- and the target individual share 1,892 cMs and that, based on this determination, the two have an M3 meiosis-separation relationship. Based on this M3 meiosis-separation relationship determination, the match determination system 100 can, for example, intelligently determine that the source individual and the target individual actually have an M4 meiosis-separation relationship (rather than an M5 meiosis-separation relationship). Further, the match determination system 100 may utilize data associated with the reconstructed data identifier to disambiguate the likely data link (or familial relationship) between the source individual and that target individual to determine that the two are first cousins.

Moreover, in contrast with existing systems that are often limited to inferring genealogical relationships based entirely (or nearly entirely) on known genealogical records and user submitted data, the match determination system 100 can more accurately determine data links (or familial relationships) using more reliable data. For instance, by integrating known genealogical records with genetic data (e.g., data identifiers, single nucleotide polymorphisms or SNPs, haplotypes, and IBD segments), the match determination system 100 is capable of cross-verifying and filling gaps in user submitted data. In other or additional instances, the match determination system 100 can employ one or more machine learning models trained on large-scale datasets of genetic data and genealogical data to analyze features (e.g., shared IBD segment lengths, counts, and/or relationships) of shared DNA between at least two individuals (or entities) to accurately predict relationships. In further contrast to existing systems, the match determination system 100 can, based on data associated with a cognate dataset, reconstruct a data identifier (e.g., genomic or genetic data) for a precursor entity (e.g., an ancestor) related to a source individual to utilize in determining data links and/or familial relationships, as discussed more below.

In addition to improving accuracy, the match determination system 100 can also improve speed and capacity to analyze, modify, and/or compare large amounts of genealogical and genetic data relative to existing systems. For example, by generating genealogical data trees from large-scale datasets without (or with relatively little) user input or manual record comparisons, the match determination system 100 can determine data link relationships and create genealogical data trees with much greater speed than many existing systems. Further, because of its demonstrated accuracy, the match determination system 100 can leverage the comparison of reconstructed data identifiers to automatedly process large amounts (e.g., terabytes or more) of genealogical and genetic data for determining data links and constructing genealogical data trees. By investing computational resources to reconstruct data identifiers for precursor entities, embodiments of the match determination system 100 achieve better accuracy in determining data links and/or familial relationships. As a result, the match determination system 100 can also generate genealogical data trees (reflecting such data links) with higher fidelity as compared to prior systems. Indeed, the match determination system 100 can analyze, modify, and/or compare data links indicated by genealogical records with data links determined from genetic data (containing millions or billions of nucleotide sequences) to, for example, quickly generate robust genealogical data trees with accurate data links and/or relationships (e.g., edges) among nodes.

As illustrated by the foregoing (and following) discussion, the present disclosure utilizes a variety of terms to describe features and advantages of the match determination system 100. Additional detail is now provided regarding the meaning of such terms. As used herein, the term "cognate" refers to an individual who shares a biological or genetic relationship with a source individual through a common ancestor. For instance, a cognate can refer to a sibling of the source individual. In the same or other embodiments, the term cognate may refer to immediate family members and/or to extended (or distant) family members or relatives. In some embodiments, the cognate's data identifiers (e.g., genomes) are analyzed in conjunction with the source individual's data identifiers to infer inheritance patterns, reconstruct data identifiers for a precursor entity, and/or identify familial connections.

Relatedly, as used herein, the term "cognate dataset" refers to a collection of data identifiers. In particular, the cognate dataset can include data identifiers for a source individual and/or one or more cognates who share a relationship (e.g., biological relationship) with the source individual through a common ancestor.

As also used herein, the term "source individual" refers to a specific individual whose genetic, genomic, and/or genealogical data serves as the primary point of reference or analysis in a dataset, comparison, or data link determination. For instance, the source individual may be the individual for whom an ancestry, a genetic condition, and/or other relationship or characteristic is being investigated or diagnosed (e.g., a proband).

As additionally used herein, the term "target individual" refers to an individual whose genetic, genomic, or genealogical data is the primary focus of a comparison, a data link determination, and/or a reconstruction process. Specifically, the target individual may be the subject of efforts to determine genetic relationships, such as a data link between the target individual and a precursor entity or a data link between the target individual and a source individual. As an example, the target individual may be the endpoint or focal subject of an analysis for comparing with a source individual (e.g., to determine a data link or a relationship between them).

As further used herein, the term "precursor entity" refers to an ancestor or predecessor whose genetic or genealogical information serves as the source or origin for a portion of the genetic data inherited by a descendant or related individuals. In some embodiments, a precursor entity can be a parent, grandparent, or other relative to a source individual and/or to one or more cognates related to the source individual. In the same or other embodiments, a precursor entity encompasses any ancestral individual whose genetic material is analyzed or inferred through data identifiers associated with their descendants or cognates, enabling for identification of inheritance events, identification of recombination breakpoints, and/or reconstruction of precursory data identifiers.

Additionally, as used herein, the term "data identifier" refers to a discrete piece of information or data that uniquely represents or characterizes a specific data point, entity, and/or feature within a dataset. In particular, a data identifier may refer to genetic, genomic, and/or genealogical data or information that defines the genetic composition of an individual at a specific locus or across a dataset. For instance, a data identifier can include a "genetic profile," which refers to a nucleotide sequence, such as a genome, a genotype, or a haplotype (or a combination thereof), that represents or defines the genetic makeup of an individual. For example, a genetic profile can include DNA data and/or other metrics extracted as part of a genetic evaluation (e.g., IBD analysis) on a genetic sample. In some cases, a genetic profile refers to or includes a target individual for a genetic evaluation, tree, or data structure. In some embodiments, data identifiers may also include metadata, such as relationships between individuals (e.g., parent-child or sibling connections), population group classifications, and/or identifiers for referencing datasets (e.g., dataset IDs or sequence IDs).

Along these lines, as used herein, the term "reconstructed data identifier" refers to a data identifier that has been inferred, derived, generated, and/or reconstructed using data associated with a cognate dataset. For instance, a reconstructed data identifier can be associated with a precursor entity and can be inferred, derived, generated, and/or reconstructed from one or more data identifiers in a cognate dataset.

Further, as used herein, the term "data match" (or "meiosis match" or "genetic match") refers to a measurable similarity or correspondence to one or more other entities' (e.g., individuals') data identifiers. Specifically, a data match can refer to a genetic match between two individuals based on the inheritance of DNA segments that have undergone meiosis, which can indicate that two individuals may be related. For example, a data match can signify that two individuals (or genetic profiles) share a certain amount of identical DNA due to inheritance from a common ancestor (e.g., a most recent common ancestor or MRCA). In some cases, the amount and length of shared DNA segments informs the degree of relatedness between individuals or genetic profiles. In certain embodiments, a data match can refer to or be represented by a data tree edge that links nodes in a data tree, signifying a match or a relationship linking two genetic profiles or individuals. In the same or other embodiments, a "precursor data match" can refer to a data match between a precursor entity and a target individual, and a "source data match" can refer to a data match between a source individual and a target individual.

Moreover, as used herein, the term "data link" refers to a link or relationship between two entities (e.g., individuals), such as familial relationships or familial ties (e.g., parent-child, siblings, cousins, etc.) or other relevant associations. In some embodiments, a data link can define or refer to a meiosis-separation relationship or a meiosis level that represents a number of (predicted) meiosis events separating two individuals or genetic profiles. For instance, a data link (e.g., a meiosis-separation relationship) can refer to an estimated number of meiosis separations through a common ancestor between the target individual and another individual (e.g., a precursor entity or a source individual). For instance, an M1 data link (or M1 match) represents a meiosis match that is separated by one meiosis event (e.g., a parent-child relationship). In addition, an M2 data link (or M2 match) represents a meiosis match that is separated by two meiosis events (e.g., a full sibling relationship). An M3 data link (or M3 match) represents a meiosis match separated by three meiosis events, such as a half-sibling, grandparent/grandchild, nibling relationship (e.g., a relationship between an individual and descendants of the individual's siblings), or pibling relationship (e.g., a relationship between an individual and siblings of the individual's ancestor). An M4 data link (or M4 match) refers to a meiosis match separated by four meiosis events, such as a first cousin, great grandparent to great grandchild, half nibling, half pibling, grand nibling relationship, or great pibling relationship. An M5 data link (or M5 match) represents a meiosis match separated by five meiosis events, such as first cousin once removed, half first cousin, half great pibling, or half grand nibling relationship. An M6 data link (or M6 match) represents a meiosis match separated by six meiosis events, such as a second cousin, first cousin twice removed, or half first cousin once removed relationship. An M7 data link (or M7 match) represents a meiosis match separated by seven meiosis events, such as a second cousin once removed, half second cousin, first cousin thrice removed, or half first cousin twice removed relationship. An M8 data link (or M8 match) represents a meiosis match separated by eight meiosis events, such as a third cousin, or a second cousin twice removed relationship. An M9 data link (or M9 match) represents a meiosis match separated by nine meiosis events, such as third cousin once removed, or second cousin thrice removed relationship. An M10 data link (or M10 match) represents a meiosis match separated by ten meiosis events. In one or more embodiments, a data link can, therefore, include, define, or otherwise correspond to one or more familial relationships between individuals and/or entities (e.g., parent/child, cousins, etc., as set forth above).

Moreover, in one or more embodiments, the match determination system 100 connects two individuals in a data tree based on the determined data link. As used herein, the term "source data link" can refer to a data link between a target individual and a source individual. In some cases, a source data link is derived, determined, or generated based on reconstructing a precursory data identifier, determining a precursor data match, and augmenting the precursor data match with a data link augmentation. Relatedly, the term "precursor data link" can refer to a data link between a target individual and a precursor entity, and the term "additional data link" can refer to a data link between a target individual and a source individual based on a source data match.

As also used herein, the term "data link augmentation" refers to a determined value, function, or metric that can be used to augment a data link. In particular, the match determination system 100 can determine a data link augmentation based on analyzing the relationship between two individuals. For instance, the match determination system 100 can analyze the meiosis-separation relationship between a source individual and a precursor entity to determine by what value a precursor data link should be augmented (e.g., increased) to reflect an accurate source data link between a target individual and the source individual.

As additionally used herein, the term "data link discrepancy" refers to an actual or probable discrepancy between two data links. For instance, the match determination system 100 can determine (or detect) a data link discrepancy between a source data link and an additional data link (e.g., between a target individual and the source individual based on a source data match). As an example, the match determination system 100 may determine that an additional data link indicates an M4 relationship and that a source data link indicates an M3 relationship. Consequently, the match determination system 100 can determine that there is a data link discrepancy between the two data links.

As further used herein, the term "data tree" refers to a genealogical data tree based on genealogical records, a genetic data tree constructed from genetic relationships, and/or a universal genealogy tree that can include a genetic data tree and/or a genealogical data tree (or a pedigree). In particular, a genetic data tree can refer to a data structure or a construct made up of nodes and edges, where the nodes represent genetic profiles or individuals (as extracted or generated by genetic IBD testing) and the edges connect the nodes, representing relationships between the genetic profiles. For example, a genetic data tree can represent genetic relatedness of genetic profiles across an entire genealogical database of a genealogical data system, including millions or billions of nodes and edges. In some cases, a genetic data tree can include or correspond to a visualization of an underlying structure that defines and depicts genetic (e.g., DNA-based) relationships among genetic profiles or individuals. Further, a genealogical data tree can refer to a family tree chart or pedigree chart that is based on genealogical records. A genealogical data tree can show, diagrammatically, family information, such as family history information, including parentage, offspring, spouses, siblings, or otherwise for any suitable number of generations and/or people, and/or data pertaining to persons represented in the chart. U.S. Pat. No. 11,429,615, entitled "Linking Individual Datasets to a Database," granted on Aug. 30, 2022, describes example embodiments of how an individual may be linked to existing family trees.

In addition, as used herein, the term "machine learning model" refers to a computer algorithm or a collection of computer algorithms that automatically improve for a particular task through iterative outputs or predictions based on use of data. For example, machine learning model can utilize one or more learning techniques to improve in accuracy and/or effectiveness. Example machine learning models include various types of neural networks, decision trees, support vector machines, and Bayesian networks. In some embodiments, the model modification system utilizes a large language machine learning model in the form of a neural network.

Relatedly, as used herein, the term "neural network" refers to a machine learning model that can be trained and/or tuned based on inputs to determine classifications, scores, or approximate unknown functions. For example, a neural network includes a model of interconnected artificial neurons (e.g., organized in layers) that communicate and learn to approximate complex functions and generate outputs based on a plurality of inputs provided to the neural network. In some cases, a neural network refers to an algorithm (or set of algorithms) that implements deep learning techniques to model high-level abstractions in data. A neural network can include various layers such as an input layer, one or more hidden layers, and an output layer that each perform tasks for processing data. For example, a neural network can include a deep neural network, a convolutional neural network, a recurrent neural network (e.g., an LSTM), a graph neural network, a transformer neural network, or a generative adversarial neural network. Upon training as described below, such a neural network may become a large language model that generates responses to prompts by interpreting prompt language, accessing additional data from content items, and executing functions indicated by prompts and/or content items.

Additional detail regarding the match determination system 100 will now be provided with reference to the figures. For example, FIG. 1 illustrates a schematic diagram of an example system environment for implementing the match determination system 100 in accordance with one or more embodiments. An overview of the match determination system 100 is described in relation to FIG. 1. Thereafter, a more detailed description of the components and processes of the match determination system 100 is provided in relation to the subsequent figures.

As shown, the environment includes server(s) 102, a client device 108, a database 106, and a network 112. Each of the components of the environment can communicate via the network 112, and the network 112 may be any suitable network over which computing devices can communicate. Example networks are discussed in more detail below in relation to FIGS. 10-11.

As mentioned above, the example environment includes a client device 108. The client device 108 can be one of a variety of computing devices, including a smartphone, a tablet, a smart television, a desktop computer, a laptop computer, a virtual reality device, an augmented reality device, or another computing device as described in relation to FIGS. 10-11. The client device 108 can communicate with the server(s) 102 and/or the database 106 via the network 112. For example, the client device 108 can receive user input from respective users interacting with the client device 108 (e.g., via the client application 110) to, for instance, search for, access, generate, modify, or share a genealogical content item and/or to interact with a data tree or a content item via a graphical user interface of the genealogical data system 104. In addition, the Match determination system 100 on the server(s) 102 can receive information relating to various searches for, or interactions with, genealogical content items, and/or user interface elements based on the input received by the client device 108.

As shown, the client device 108 can include a client application 110. In particular, the client application 110 may be a web application, a native application installed on the client device 108 (e.g., a mobile application, a desktop application, etc.), or a cloud-based application where all or part of the functionality is performed by the server(s) 102. Based on instructions from the client application 110, the client device 108 can present or display information, including a user interface such as a data tree interface (e.g., an interface for managing data link discrepancies) and/or some other graphical user interface.

As illustrated in FIG. 1, the example environment also includes the server(s) 102. The server(s) 102 may generate, track, store, process, receive, and transmit electronic data, such as genetic data (e.g., data identifiers), data matches, data links, various algorithms, and/or data trees. For example, the server(s) 102 may receive data from the client device 108 in the form of a request to view or add new genomic data to a data tree. In addition, the server(s) 102 can transmit data to the client device 108 in the form of a data tree interface depicting a data tree (including newly added genomic data). Indeed, the server(s) 102 can communicate with the client device 108 to send and/or receive data via the network 112. In some implementations, the server(s) 102 comprise(s) a distributed server where the server(s) 102 include(s) a number of server devices distributed across the network 112 and located in different physical locations. The server(s) 102 can comprise one or more content servers, cloud computing servers, application servers, communication servers, web-hosting servers, machine learning server, and other types of servers.

As shown in FIG. 1, the server(s) 102 can also include the match determination system 100 as part of a genealogical data system 104. The genealogical data system 104 can communicate with the client device 108 to perform various functions associated with the client application 110 such as performing genetic evaluations, determining data matches, managing user accounts, managing genealogical data, managing data trees, managing genealogical content items, and facilitating user interaction with, and sharing of, the data trees and/or genealogical content items. Indeed, the genealogical data system 104 can include a network-based cloud storage system to manage, store, and maintain genetic data and genealogical data user accounts. In some cases, the genealogical data system 104 can utilize genealogical data across various content items and user accounts to generate and maintain a universal genealogy tree that reflects the relatedness or consanguinity between nodes corresponding to all user accounts and other individuals indicated by stored genealogical content items. In some embodiments, the match determination system 100 and/or the genealogical data system 104 utilize the database 106 to store and generate a universal data tree defining genetic relationships in addition to the universal genealogy tree defining relationship extrapolated from various content items and other (non-genetic) data.

As further illustrated in FIG. 1, the genealogical data system 104 includes a database 106 that stores genetic data, such as genetic profiles, meiosis matches, relationship clusters, and other data tree data. In particular, the match determination system 100 stores the genetic data to generate a data tree. For instance, the match determination system 100 generates and maintains a match database (e.g., as part of or as a label for the database 106) that stores data match data, such as data links between data identifiers.

Although FIG. 1 depicts the match determination system 100 located on the server(s) 102, in some implementations, the match determination system 100 may be implemented by (e.g., located entirely or in part on) one or more other components of the environment. For example, the match determination system 100 may be implemented in whole or in part by the client device 108. For example, the client device 108 and/or a third-party system can download all or part of the match determination system 100 (e.g., a match database and/or one or more relationship clusters) for implementation independent of, or together with, the server(s) 102.

In some implementations, though not illustrated in FIG. 1, the environment may have a different arrangement of components and/or may have a different number or set of components altogether. For example, the client device 108 may communicate directly with the match determination system 100, bypassing the network 112. As another example, the environment may include multiple client devices, each associated with a different user account. In addition, the environment can include the database 106 located external to the server(s) 102 (e.g., in communication via the network 112) or located on the server(s) 102 and/or on the client device 108.

Figure 2:
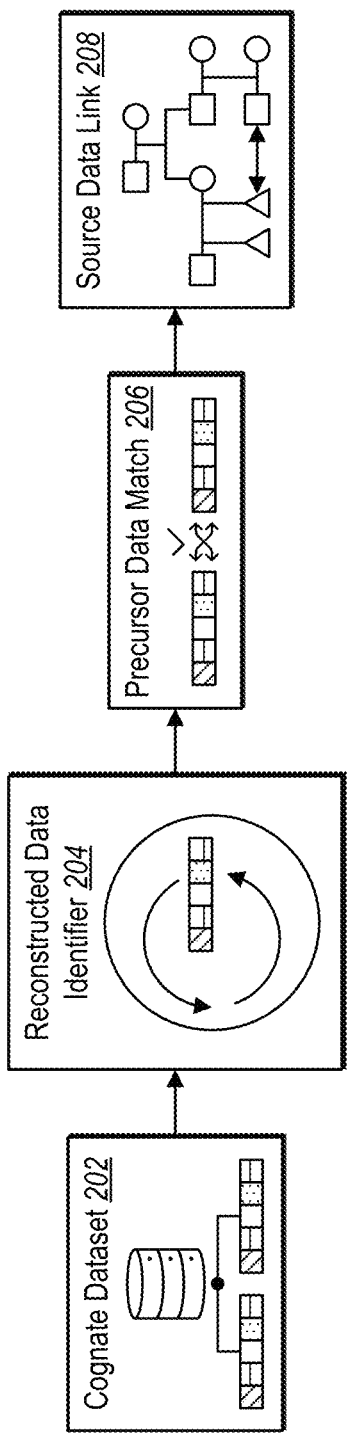
FIG. 2 illustrates an example diagram of determining a source data link based on a precursor data match in accordance with one or more embodiments.

As expressed above, the match determination system 100 can determine a source data link between individuals and/or entities. For instance, the match determination system 100 can determine a source data link between a target individual and a source individual. FIG. 2 illustrates an example diagram of determining a source data link based on a precursor data match in accordance with one or more embodiments. Additional detail regarding the acts and processes introduced in relation to FIG. 2 is provided thereafter with reference to subsequent figures.

As illustrated in FIG. 2, the match determination system 100 receives or identifies a cognate dataset 202. In particular, the match determination system 100 can receive or identify the cognate dataset 202 that includes data identifier(s) for a source individual and/or data identifier(s) for each of one or more cognates related to the source individual. In some cases, the match determination system 100 can receive or identify the cognate dataset 202 that does not include data identifier(s) for the source individual and that includes only data identifier(s) for each of the one or more cognates related to the source individual. In some cases, the match determination system 100 accesses the cognate dataset 202 from a database (e.g., the database 106) of genetic data within the genealogical data system 104.

As also illustrated in FIG. 2, the match determination system 100 generates a reconstructed data identifier 204. Specifically, the match determination system 100 can generate the reconstructed data identifier 204 for a precursor entity corresponding to the source individual. For instance, the precursor entity can be a parent, grandparent, or other relative to the source individual.

In one or more embodiments, the match determination system 100 generates the reconstructed data identifier 204 from the cognate dataset 202. In particular, the match determination system 100 can phase each data identifier in the cognate dataset 202 to generate a pair of phased data segments (e.g., chromosome copies) for each individual (e.g., the source individual and/or one or more cognates) in the cognate dataset 202. Upon phasing each data identifier, the match determination system 100 can compare the phased data segments of the cognate dataset 202 to determine (or identify), for each individual in the cognate dataset 202, at least one phased data segment (e.g., haplotype) that is inherited from a precursor entity. Based on this determination, the match determination system 100 can extract, for each individual in the cognate dataset 202, the at least one phased data segment (e.g., haplotype) that is inherited from the precursor entity to generate (or form) a set of cognate phased data segments (e.g., a set of sibling chromosome copies) inherited from the precursor entity. In some embodiments, the match determination system 100 can determine data exchange breakpoints (e.g., recombination breakpoints) in the set of cognate phased data segments by identifying data mismatch locations amongst the phased data segments. In the same or other embodiments, the match determination system 100 generates the reconstructed data identifier 204 for the precursor entity based on the determined data exchange breakpoints.

As further illustrated in FIG. 2, the match determination system 100 generates a precursor data match 206 between the precursor entity and a target individual. Specifically, the match determination system 100 can utilize the reconstructed data identifier 204 for the precursor entity and a data identifier for the target individual to generate the precursor data match 206. In some instances, the match determination system 100 generates the precursor data match 206 based on determining that the precursor entity and the target individual share a certain amount (e.g., higher than a threshold) of identical DNA due to inheritance from a common ancestor (e.g., a most recent common ancestor or MRCA). Further, the match determination system 100 can, in some cases, generate a plurality of precursor data matches between the precursor entity and the target individual.

Additionally, as illustrated in FIG. 2, the match determination system 100 determines a source data link 208 between the target individual and the source individual. In particular, the match determination system 100 can determine a precursor data link between the precursor entity and the target individual based on the precursor data match 206. To elaborate, upon generating the precursor data match 206, the match determination system 100 determines a meiosis-separation relationship (or a meiosis level) between the precursor entity and the target individual. For example, the match determination system 100 can determine the meiosis-separation and/or a familial relationship by predicting the number of meiosis separations through a common ancestor between the precursor entity and the target individual.

As part of this process, in some embodiments, the match determination system 100 can utilize the reconstructed data identifier 204 and/or the precursor data match 206 to determine genetic information relating to a source individual, including informed predictions or probabilities for which portions of genetic data correspond to heritable characteristics of the source individual's genome (e.g., to better indicate which portions of the source individual's genome are passed down from the precursor entity). Indeed, the match determination system 100 uses the reconstructed data identifier 204 of the precursor entity, along with the genetic information of the precursor data match 206, to disambiguate the source data link 208 from among a set of candidate data links (e.g., by updating or augmenting its probability or likelihood among the candidate data links). As an example, the match determination system 100 may utilize the reconstructed data identifier 204 and/or the precursor data match 206 to determine that the most likely (or highest probability) data link between the source individual and the target individual (i.e., the source data link 208) corresponds to a familial relationship of grandchild-grandparent.

In one or more embodiments, the match determination system 100 determines a data link augmentation to combine with the precursor data link to thereby determine the source data link 208. For instance, the match determination system 100 can determine the data link augmentation by analyzing a meiosis-separation relationship between a source individual and a precursor entity to determine by what value the precursor data link should be augmented (e.g., increased) to reflect an accurate source data link 208.

Figure 3:
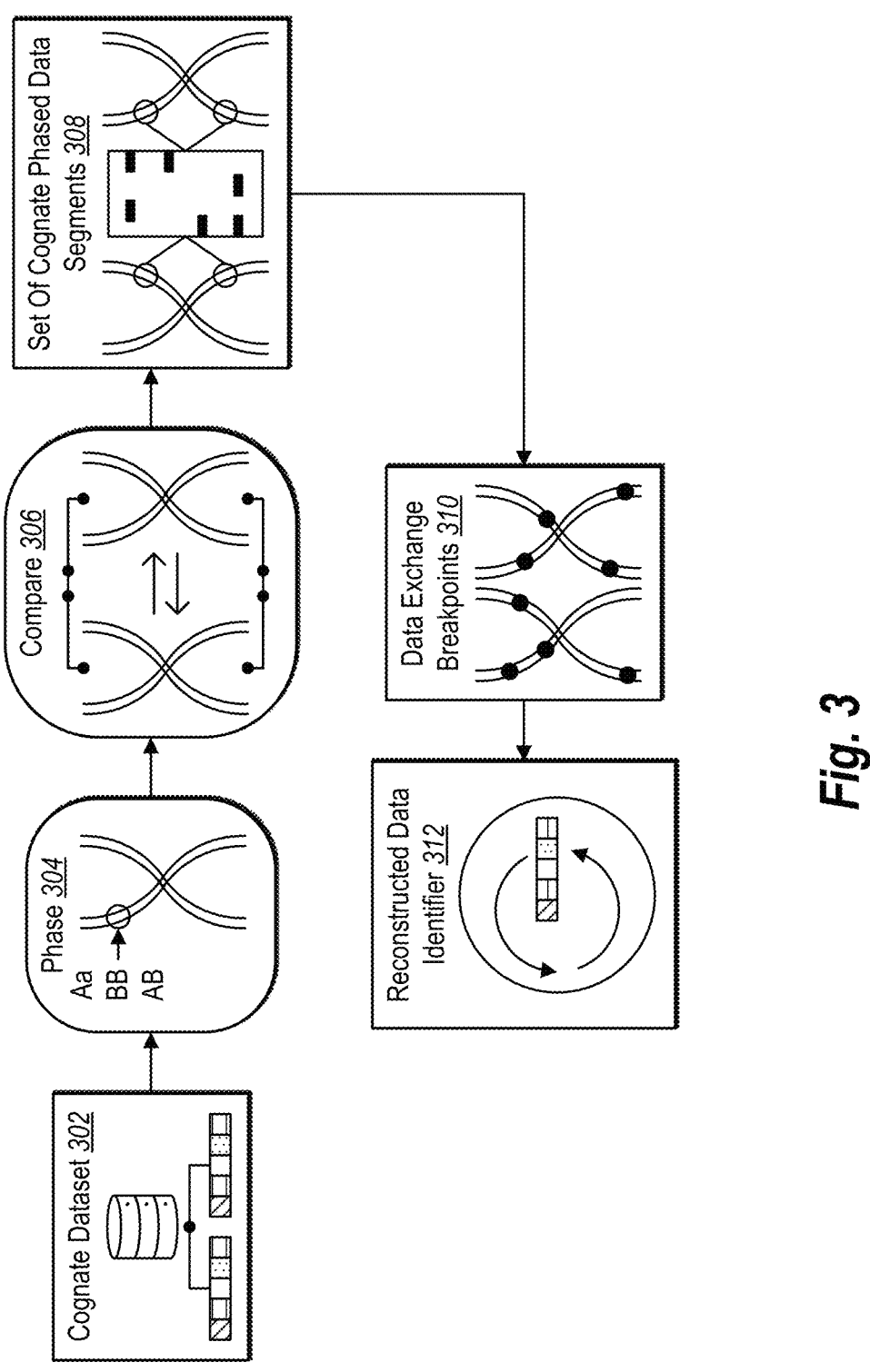
FIG. 3 illustrates an example diagram of a process for generating a reconstructed data identifier for a precursor entity in accordance with one or more embodiments.

As expressed above, the match determination system 100 can generate a reconstructed data identifier for a precursor entity of a source individual. In particular, the match determination system 100 can utilize a cognate dataset to generate the reconstructed data identifier. FIG. 3 illustrates an example diagram of a process for generating a reconstructed data identifier for a precursor entity in accordance with one or more embodiments. In one or more implementations, generating a reconstructed data identifier (e.g., reconstructing a precursory inheritance dataset) is as described by Clinton C. Mason et al. in U.S. patent application Ser. No. 18/927,700, entitled RECONSTRUCTING A PRECUR-SORY INHERITANCE DATASET, filed Oct. 25, 2024, which is hereby incorporated by reference in its entirety.

As illustrated in FIG. 3, the match determination system 100 receives, generates, identifies, or accesses a cognate dataset 302. Specifically, the match determination system 100 can receive the cognate dataset 302 that includes a data identifier for a source individual and/or data identifiers for one or more cognates related to the source individual. In some embodiments, the one or more cognates can corre-spond to one or more siblings of the source individual. The source individual and/or the one or more cognates may share the same pair of parents (e.g., inherit their genetic data from the same two parents, including paternal genetic data and maternal genetic data). Each of the data identifiers in the cognate dataset 302 can contain data based on the whole or on portions of the respective genomes of the source indi-vidual and/or the one or more cognates. In some embodi-ments, the cognate dataset 302 may be in the form of diploid data that includes alleles present on two copies of a chro-mosome for a sibling. The cognate dataset 302 may be stored in a genetic data store.

As also illustrated in FIG. 3, the match determination system 100 performs the act 304 of phasing data identifiers in the cognate dataset 302. In particular, the match deter-mination system 100 can perform the act 304 to generate a pair of phased data segments for the source individual and/or the one or more cognates. For example, the match determi-nation system 100 may phase a data identifier to generate a pair of haplotypes for each of the source individual and/or the one or more cognates. In some embodiments, the match determination system 100 may perform a genome-wide phasing of each genetic dataset to generate a pair of chro-mosome copies for each of the source individual and/or the one or more cognates. The match determination system 100 may use any suitable phasing algorithm to perform the phasing, which may include genome-wide phasing. For example, the match determination system 100 may utilize an IBD-phasing algorithm of a phasing engine to generate a phasing result that has a long genomic distance accuracy and cross-chromosome accuracy in terms of haplotype separa-tion and correlation. For each of the source individual and/or the one or more cognates, a pair of chromosome copies may correspond to a diploid dataset that may be phased into one pair of haploid data, that is, two sets of haploid data. For example, one set of haploid data corresponds to the genetic dataset from a first parent (e.g., paternal) and the other set of haploid data corresponds to the genetic dataset from the second parent (e.g., maternal). In some embodiments, the match determination system 100 may separate the haploid data of the first parent from those of the second parent.

As additionally illustrated in FIG. 3, the match determi-nation system 100 performs the act 306 to compare phased data segments. Specifically, the match determination system 100 performs the act 306 to identify, from among the phased data segments, one or more phased data segments that are inherited from a precursor entity (e.g., a father or a mother). For example, the match determination system 100 may compare the chromosome copies of data identifiers in the cognate dataset 302 to identify a chromosome copy that is inherited from a precursor entity for the source individual and/or the one or more cognates. For the source individual and/or the one or more cognates, each chromosome may correspond to a haplotype or part of a haplotype generated by a long-distance phasing algorithm.

As an example, for three siblings S1, S2, and S3 associ-ated with the cognate dataset 302, the haplotypes correspond to six sets of haplotype data. To determine which three of the six sets of haplotype data are inherited from a shared precursor entity (e.g., a same parent), the match determina-tion system 100 may compare the six sets of haplotype data to determine, for example, the highest correlation among the six sets of haplotype data. In some embodiments, the match determination system 100 identifies matched portions of haplotype data between two siblings associated with the cognate dataset 302 by comparing and identifying identical alleles at SNP sites in the phased haplotypes between two siblings. The match determination system 100 may deter-mine three sets of haplotype data, one from each sibling, that are correlated and/or inherited from a same parent. Because the haplotypes may be from siblings who inherit the hap-lotypes from the same parents, three of the six haplotypes may share long stretches of identical nucleotide sequences. Similarly, the other three of the six haplotypes may also share long stretches of identical nucleotide sequences. Accordingly, in some cases, the six haplotypes are separated into two groups (e.g., for both parents).

As further illustrated in FIG. 3, the match determination system 100 can generate a set of cognate phased data segments 308 that are inherited from a precursor entity (e.g., a father or a mother). In particular, the match determination system 100 can generate the set of cognate phased data segments 308 by extracting, for the source individual and/or the one or more cognates, phased data segments that are inherited from a particular precursor entity. For instance, the match determination system 100 may extract, for the source individual and/or the one or more cognates, a chromosome copy that is inherited from a parent to form a set of sibling chromosome copies that are inherited from the parent.

Additionally, as illustrated in FIG. 3, the match determi-nation system 100 can determine data exchange breakpoints 310 in the set of cognate phased data segments 308. Spe-cifically, the match determination system 100 can determine the data exchange breakpoints 310 by determining (or identifying) locations of change in data agreement among the phased data segments in the set of cognate phased data segments 308. For instance, the match determination system 100 determines the data exchange breakpoints 310 by iden-tifying recombination breakpoints in the set of sibling chro-mosome copies. Because a pair of haplotypes for each precursor entity (e.g., a mother and a father) are often recombined and passed uniquely to each child (e.g., the source individual and/or the one or more cognates) to form corresponding haplotypes for each child, the extracted hap-lotypes from siblings may not be identical to the haplotypes of the precursor entity or to each other. Accordingly, in some embodiments, a recombination breakpoint may refer to a location at which such a change in agreement (e.g., a divergence) of haplotypes occurs among the set of cognate phased data segments 308.

Furthermore, as illustrated in FIG. 3, the match determi-nation system 100 generates a reconstructed data identifier 312 (or reconstructs a data identifier) for a precursor entity. In particular, the match determination system 100 can gen-erate a reconstructed data identifier 312 for a precursor entity based on the data exchange breakpoints 310. For example, the match determination system 100 may recon-struct a pair of precursor entity haplotypes based on one or more identified recombination breakpoints (e.g., one or more segments of a haplotype that fall between two adjacent recombination breakpoints) and assigning each identified portion of haplotypes for association with a parent of the precursor entity, that is, with a grandparent of the source individual and/or the one or more cognates. In some embodiments, the match determination system 100 may assign identified portions of haplotypes for association with a grandparent based on a voting process.

In the same or other embodiments, the match determination system 100 rearranges grouped portions of haplotypes related to a first grandparent (e.g., a grandmother) to reconstruct the haplotypes related to the first grandparent. Similarly, the match determination system 100 may rearrange grouped portions of haplotypes related to a second grandparent (e.g., a grandfather) to reconstruct the haplotypes related to the second grandparent. In some cases, the match determination system 100 may rearrange the portions of haplotypes based on the sequence of alleles at the SNP sites. Based on the reconstructed haplotypes related to the first grandparent and the second grandparent, the match determination system 100 can reconstruct both chromosome copies (e.g., two haplotypes) for a precursor entity (e.g., a father). A similar process may be used to reconstruct both chromosome copies for the other precursor entity (e.g., a mother) of the source individual and/or the one or more cognates.

In some embodiments, reconstruction may be limited locally within a chromosome. In the same or other embodiments, the reconstruction may be a genome-wide reconstruction of the precursor entity genome or a measurable portion of the precursor entity genome occurring across multiple or all chromosomes. Further, in some cases, experimenters have demonstrated that (depending on the number of cognates and/or the amount of cognate data available) the match determination system 100 generates the reconstructed data identifier 312 (or reconstructs) with greater than a 99% accuracy level, and in some cases effectively 100% accuracy.

Figure 4:
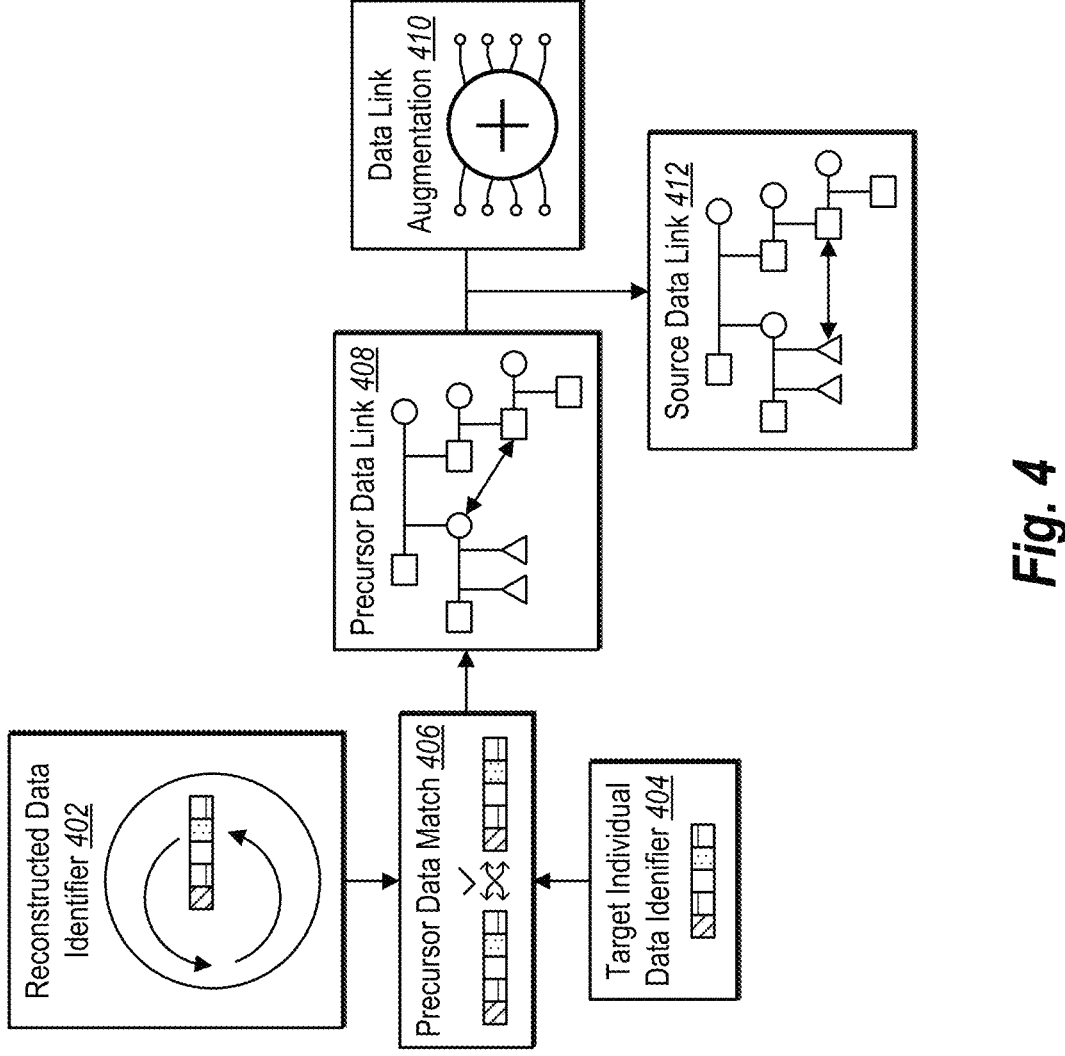
FIG. 4 illustrates an example diagram of a process for determining a source data link between a target individual and a source individual in accordance with one or more embodiments.

As expressed above, the match determination system 100 can determine a source data link between a target individual and a source individual. In particular, the match determination system 100 can utilize a precursor data match between a precursor entity and a target individual to determine the source data link. FIG. 4 illustrates an example diagram of a process for determining a source data link between a target individual and a source individual in accordance with one or more embodiments. In one or more implementations, generating a data match (e.g., a genetic match) and/or determining a data link (e.g., a meiosis separation relationship) is as described by Ross E. Curtis et al. in U.S. patent application Ser. No. 18/924,937, entitled SYSTEMS AND METHODS FOR DETERMINING DATA-ORIGIN LINKS BETWEEN NAMED ENTITIES, filed Oct. 23, 2024, which is hereby incorporated by reference in its entirety.

As illustrated in FIG. 4, the match determination system 100 can generate (or receive) a reconstructed data identifier 402 for a precursor entity who is related to a source individual and/or a target individual data identifier 404 for a target individual. In some embodiments, the match determination system 100 generates the reconstructed data identifier 402, as explained above. In the same or other embodiments, the match determination system 100 receives the reconstructed data identifier 402 and/or the target individual data identifier 404.

As also illustrated in FIG. 4, the match determination system 100 can generate a precursor data match 406 between the precursor entity and the target individual. In particular, the match determination system 100 can utilize the reconstructed data identifier 402 and the target individual data identifier 404 to generate the precursor data match 406.

For example, the match determination system 100 generates the precursor data match 406 based on determining that the precursor entity and the target individual share a certain amount of identical DNA due to inheritance from a common ancestor (e.g., a most recent common ancestor or MRCA). In the same or other embodiments, the match determination system 100 generates the precursor data match 406 based on determining that the precursor entity and the target individual share a number of identical-by-descent (IBD) segments and/or cumulative or segment-specific shared cM that is higher than a threshold. For instance, the match determination system 100 may generate the precursor data match 406 by analyzing the data identifiers (e.g., genomes and/or genotypes) of the precursor entity and the target individual to identify and compare single nucleotide polymorphisms (SNPs) in an identity-by-descent approach. Further, the match determination system 100 can, in some cases, generate a plurality of precursor data matches between the precursor entity and the target individual.

As additionally illustrated in FIG. 4, the match determination system 100 determines a precursor data link 408 between the precursor entity and the target individual. Specifically, the match determination system 100 determines the precursor data link 408 based on the precursor data match 406. To elaborate, upon generating the precursor data match 406, the match determination system 100 determines a meiosis-separation relationship between the precursor entity and the target individual. For example, the match determination system 100 can determine the meiosis-separation relationship by predicting the number of meiosis separations (e.g., a degree of match) through a common ancestor between the precursor entity and the target individual.

In some embodiments, and as seen below in Table 1, the match determination system 100 can determine a data link or a number of meiosis-separation events, an abbreviation for the data link, and possible relationships between two individuals corresponding to the determined data link. The degree of meiosis separation may be denoted as M1, M2, M3, M4, etc., which respectively signifies a first degree of meiosis separation (or a meiosis match that is separated by one meiosis event), a second degree of meiosis separation (or a meiosis match that is separated by two meiosis events), and so on. As an example, the match determination system 100 may make an initial determination that the precursor entity and the source individual have an M3 relationship (or M3 match) on the basis of the cM of IBD segments shared between the target individual and target relative falling within a predetermined range of cM shared for M3 relationships.

TABLE 1

| Number of Meiosis-Separation Events | Abbreviation | Possible Relationships |
|---|---|---|
| One-meiosis-event relationship | M1 | Parent-child |
| Two-meiosis-event relationship | M2 | Full Siblings |
| Three-meiosis-event relationship | M3 | Half-sibling, Grandparent, Nibling, Pibling |
| Four-meiosis-event relationship | M4 | First cousin, Great grandparent, Half Pibling, Great Pibling |
| Five-meiosis-event relationship | M5 | First cousin once removed, Half first cousin, Great-great Pibling, Great-great grandparent, Half great Pibling |

TABLE 1-continued

| Number of Meiosis-Separation Events | Abbre-viation | Possible Relationships |
|---|---|---|
| Six-meiosis-event relationship | M6 | Second cousin, First cousin twice removed, Half first cousin once removed, Half two-generation Pibling, Three-generation grandparent |
| Seven-meiosis-event relationship | M7 | Second cousin once removed, Half second cousin, First cousin thrice removed, Half first cousin twice removed, Four-generation Pibling, Half three-generation Pibling, Four-generation grandparent |
| Eight-meiosis-event relationship | M8 | Third cousin, Second cousin twice removed, Half second cousin once removed, First cousin four times removed, Half first cousin three times removed, Five-generation Pibling, Half four-generation Pibling, Five-generation grandparent |
| Nine-meiosis-event relationship | M9 | Third cousin once removed, Half third cousin, Second cousin thrice removed, Half second cousin twice removed, First cousin five times removed, Half first cousin four times removed, Six-generation Pibling, Half five-generation Pibling |
| Ten-meiosis-event relationship | M10 | Fourth cousin, Third cousin twice removed, Half third cousin once removed, Second cousin four times removed, Half second cousin thrice removed, First cousin six times removed, Half first cousin five times removed, Seven-generation Pibling, Half six-generation Pibling |

In one or more embodiments, the match determination system 100 can determine the precursor data link 408 by identifying the most-recent common ancestor (MRCA). In particular, when the family relationships of the precursor entity and the target individual are known, the match determination system 100 may determine the precursor data link 408 by identifying the MRCA between the precursor entity and the target individual. For example, the estimated degree of relatedness between first cousins may be M4 because the MRCA in this example is one of the grandparents. The meiosis separations include (i) descendant A-parent A, (ii) parent A-common grandparent, (iii) common grandparent-parent B, and (iv) descendant B-parent B. In another example, the estimated degree of relatedness between an aunt-niece relationship may be M3 because the MRCA here is the parent of the aunt (grandparent of the niece), with meiosis separations that include (i) niece-parent, (ii) parent to grandparent, and (iii) grandparent to aunt.

In the same or other embodiments, the match determination system 100 can determine the precursor data link 408 based on shared IBD segments. Specifically, when the precise familial relationships of the precursor entity and the target individual are unknown but the genetic data of both individuals and/or entities are available, the match determination system 100 can determine (or predict) the precursor data link 408 based on the amount of IBD segments shared between the precursor entity and the target individual. For example, the computing server 130 may determine which degree of separation the total length of shared DNA (e.g. in cM) and/or the total number of shared segments between the two individuals corresponds to.

In some cases, the letter "w" denotes the cumulative or segment-specific length of the shared IBD segments between a pair of descendants in a pairwise genetic relationship. These IBD segments represent portions of DNA that are determined to have been inherited from a common ancestor. The length of these shared IBD segments may be used to calculate relationship scores, which are then further analyzed to determine the degree of relatedness between individuals (e.g., the precursor entity and the target individual) within a family tree. In some instances, the letter "m" denotes the estimated degree of relatedness between a pair of descendants (e.g., the precursor entity and the target individual) in a pairwise genetic relationship. The degree of relatedness may be determined based on an estimated number of meiosis separations between the pairs of descendants through a common ancestor.

In at least one embodiment, the value, m, may be used in conjunction with the length of shared IBD segments (denoted by the value w) to calculate relationship scores, which can be used to determine the overall confidence level of relatedness between individuals within a family tree. In some embodiments, the relationship score may correspond to a conditional probability of the estimated degree of relatedness, m, given the length of the shared IBD segments, w. The conditional probability may be denoted as Pr(m|w). In particular, Pr(m|w) can denote the conditional probability of the estimated degree of relatedness 'm,' given the length of the shared IBD segments 'w.' In other words, Pr(m|w) can represent the probability of observing a particular degree of relatedness 'm' between two individuals when the length of their shared IBD segments is 'w.' This conditional probability can play a crucial role in determining relationship scores, which may be used to assess overall confidence levels of relatedness between individuals within a family tree.

In some embodiments, the meiosis-separation relationship between two individuals may be directly based on the bucket in which the total length of shared IBD segments of the genetic data associated with the precursor entity and the target individual fall. For example, M4 relationships may have a range between X cM and Y cM, and if the total length of shared IBD segments is between X and Y, the match determination system 100 may determine that the meiosis-separation relationship is M4.

In some situations, some of the genetic matches may have sufficient family-tree data available between the precursor entity and the target individual. In such a case, the match determination system 100 may additionally or alternatively determine the meiosis-separation relationship based on family data. The evaluation of evidence can depend on how m, the tree relationship, is calculated. For a simple case—such as when there is a full relationship with only one pair of observed common ancestors—m is the number of hops between the two individuals (e.g., 1st cousins are M4). A "hop" can be considered a reproductive event. Each hop can represent a single generational connection between two individuals, such as a parent-child relationship. The number of hops helps estimate the number of meiosis separations between individuals through their common ancestor(s).

In at least one embodiment, more complicated relationships can be fit into the framework below. (1) For any half relationship between two individuals, the match determination system 100 may use the m(x+1) distribution. (2) In some cases, inbreeding or endogamy adds another path to the common ancestor couple. This can act the same as if there was a completely different ancestor. For example, m8wm6 mg (m8 relationship with an m6 marriage in one of the lines) is the same as m8+m8. If the cousin marriage happens on a path that is longer than the closest path, then that can be reflected accordingly (e.g., m8+m9). (3) In some instances, 2 m(x) is equal to m(x−1). That is, m8+m8=m7. (4) In some embodiments, m(x)+m(x+1) is equal to a distribution halfway between the m(x) and m(x−1) distributions. In such cases, the higher score between the distributions should be used. (5) In some cases, m(x)+m(x+y) where y>1 is very close to the m(x) distribution. This distribution or the max between the m(x) and m(x−1) distributions could be used.

For example, consider the following relationship:

$$m7 + m8 + m8wm7mg + m9 + m9wm6mg + m10 + m10 + m11$$

The above relationship can be simplified by first expanding the marriage inbreeding relationships:

$$m7 + m8 + m8 + m9 + m9 + m9 + m9 + m10 + m10 + m11$$

The relationship can be further simplified by considering the combinations of relationships, highest relationships first:

$$m7 + m8 + m8 + m9 + m9 + m9 + m9 + m9 + m11$$

$$m7 + m8 + m8 + m8 + m9 + m9 + m9 + m11$$

$$m7 + m8 + m8 + m8 + m8 + m9 + m11$$

$$m7 + m7 + m8 + m8 + m9 + m11$$

$$m7 + m7 + m7 + m9 + m11$$

$$m6 + m7 + m9 + m11$$

The relationship distribution is expected to be between the m6 and m7 distributions. The match determination system 100 may run both m6-specific and m7-specific trained models and take the maximum score.

In one or more embodiments, the match determination system 100 determines the estimated degree of relatedness based on an estimated number of meiosis separations between the pairs of descendants in a particular pairwise genetic relationship. In particular, the match determination system 100 may count the estimated number of meiosis separations through a common ancestor between the precursor entity and the target individual. For instance, the match determination system 100 may identify the MRCA between the precursor entity and the target individual. As an example, the estimated degree of relatedness between first cousins may be four because the MRCA in this example is one of the grandparents. The meiosis separations include (i) descendant A-parent A, (ii) parent A-common grandparent, (iii) common grandparent-parent B, and (iv) descendant B-parent B. In another example, the estimated degree of relatedness between an aunt-niece relationship may be three because the MRCA here is the parent of the aunt (grandparent of the niece).

In some embodiments, the values of the conditional probability may be determined based on Bayes' Law. For example, Pr(m|w)=Pr(w|m)*Pr(m)/Pr(w).

In some cases, the formula Pr(m|w)=Pr(w|m)*Pr(m)/Pr(w) represents the relationship between the conditional probabilities:

Pr(m|w) is the conditional probability of the estimated degree of relatedness 'm' given the length of shared IBD segments 'w.'

Pr(w|m) is the conditional probability of observing the length 'w' of the shared IBD segments given the degree of relatedness 'm.'

Pr(m) is the prior probability of the degree of relatedness 'm' occurring.

Pr(w) is the probability of observing the length 'w' of the shared IBD segments.

By applying Bayes' Law to these probabilities, the match determination system 100 can calculate Pr(m|w), the probability of a particular degree of relatedness 'm' given the observed IBD segment length 'w.' The match determination system 100 can the use the probability to determine the relationship scores, which can aid in assessing the overall confidence level of relatedness between the precursor entity and the target individual within a family tree.

As further illustrated in FIG. 4, the match determination system 100 determines (or generates) a data link augmentation 410 that can be used to augment the precursor data link 408. In particular, the match determination system 100 determines the data link augmentation 410 by analyzing the meiosis-separation relationship between the source individual and the precursor entity to determine by what value the precursor data link 408 should be augmented (e.g., increased) to reflect an accurate source data link 412 between a target individual and the source individual. For example, the match determination system 100 determines a one-generation hop between a precursor data identifier and a source data identifier and thus determine that the data link augmentation is a +1 modification to the precursor data link 408.

Additionally, as illustrated in FIG. 4, the match determination system 100 can determine (or generate) the source data link 412. In particular, the match determination system 100 may combine the precursor data link 408 and the data link augmentation 410 to determine (or generate) the source data link 412. As an example, the match determination system 100 may determine that the meiosis-separation relationship between the precursor entity and the source individual is an M1 relationship. Based on this determination, the match determination system 100 can determine that the data link augmentation corresponds to a value of M1. Further, upon determining that the meiosis-separation relationship between the precursor entity and the target individual is, for example, an M4 relationship, the match determination system 100 can augment (or sum) the M4 relationship with the M1 data link augmentation value (e.g., M4+M1) to determine that the source data link between the target individual and source individual is an M5 relationship.

In one or more embodiments, the match determination system 100 can determine a familial relationship from, or in addition to, the source data link 412. In particular, the match determination system 100 can utilize the reconstructed data identifier 402, the precursor data match 406, and/or the precursor data link 408 to incorporate data (e.g., IBD segments, cM overlap, or other genetic features) or information about the heritable characteristics of the source individual's genome, thereby allowing the match determination system 100 to disambiguate a likely relationship between the source individual and a target individual from the noise of possible relationships (e.g., at a given meiosis level). For example, by utilizing the reconstructed data identifier 402, the precursor data match 406, and/or the precursor data link 408 (and/or data or information associated with one or more of these), the match determination system 100 can rule out relationships between the source individual and the target individual that are inconsistent with inheritance patterns.

In the same or other embodiments, the match determination system 100 may input extracted data (including features, such as shared IBD segment lengths, counts, and/or relationships) or information associated with the reconstructed data identifier 402, the precursor data match 406, and/or the precursor data link 408 into a trained machine learning model to determine a familial relationship for the source data link 412. For instance, the machine learning model may include a regression model, a gradient-boosting machine, a random forest classifier, a support vector machine, a neural network, and/or a model trained by an unsupervised approach. The match determination system 100 may also connect the target individual and the source individual in a genealogical data tree (e.g., a family tree) based on the determined familial relationship. As an example, for an M3 relationship, the familial relationship for the source data link 412 between the source individual and the target individual may be grandparent/grandchild, half siblings, nibling, or pibling.

Figure 5:
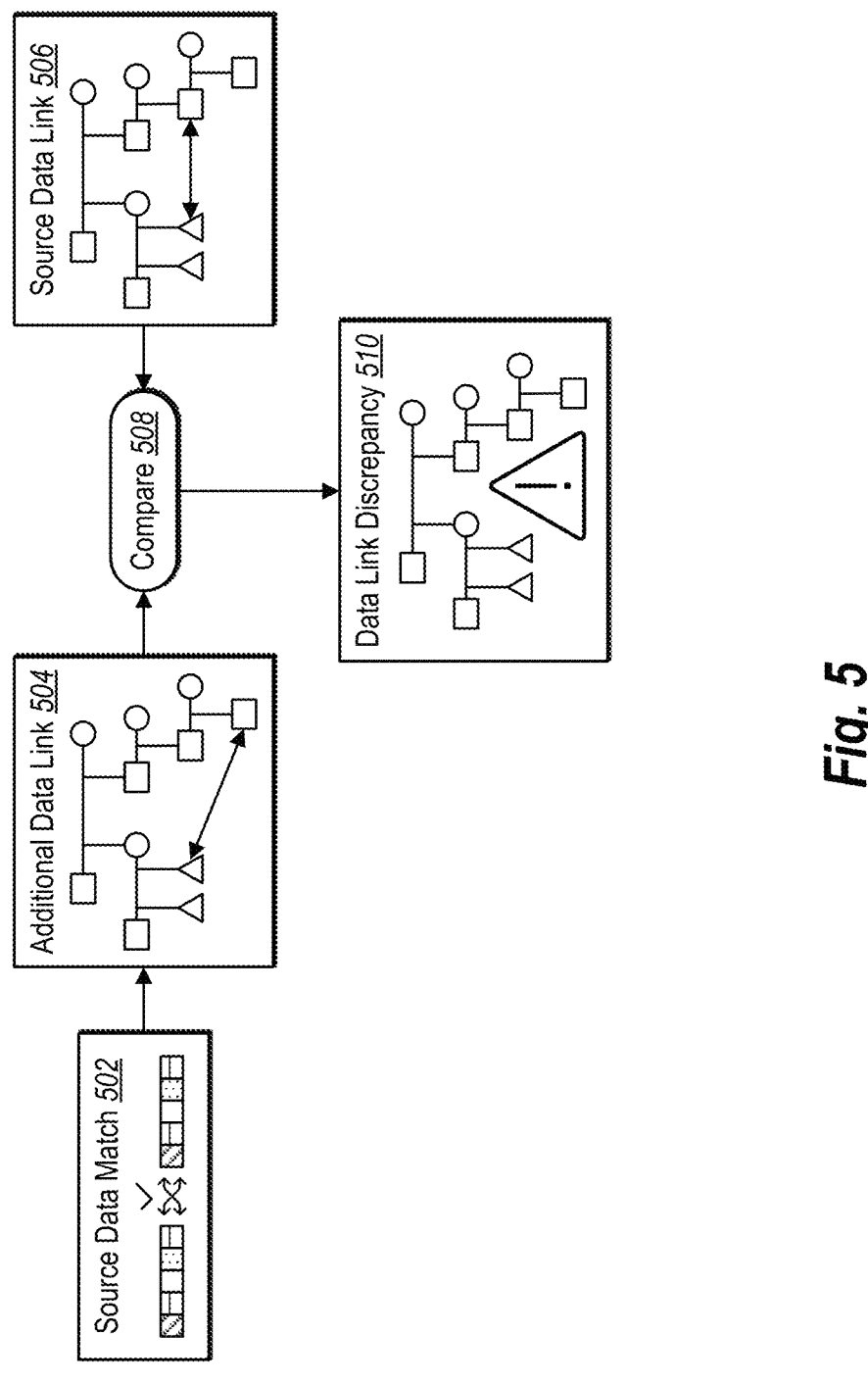
FIG. 5 illustrates an example diagram of a process for determining a data link discrepancy between a source data link and an additional data link in accordance with one or more embodiments.

As expressed above, the match determination system 100 can determine (or detect) a data link discrepancy between two data links. In particular, the match determination system 100 can determine a source data link and an additional data link and, further, that that there is a data link discrepancy between the two data links. FIG. 5 illustrates an example diagram of a process for determining a data link discrepancy between a source data link and an additional data link in accordance with one or more embodiments.

As illustrated in FIG. 5, the match determination system 100 can generate a source data match 502 between a source individual and a target individual. Specifically, in some cases, the match determination system 100 may generate the source data match 502 rather than or in addition to a precursor data match between the precursor entity and the target individual. In at least one embodiment, the match determination system 100 generates the source data match 502 using the data match process described, for example, in relation to FIG. 4 and/or in U.S. patent application Ser. No. 18/924,937, incorporated by reference above. For instance, the match determination system 100 compares genetic data markers (e.g., IBD segments) to determine cM overlap (and/or other genetic similarities) between a source individual and a target individual.

As also illustrated in FIG. 5, the match determination system 100 determines an additional data link 504 between the target individual and the source individual. Similar to the process described above in relation to FIG. 4 for determining the precursor data link 408 from the precursor data match 406, the match determination system 100 can determine the additional data link 504 based on the source data match 502. To elaborate, in some cases, the match determination system 100 determines the additional data link 504 (e.g., a data link or familial relationship through a common ancestor) based on the cM overlap (e.g., a number of shared cMs) and/or other genetic data similarity between a source individual and a target individual, as indicated by the source data match 502.

In some embodiments, the match determination system 100 can receive an indication of the additional data link 504 from a client device. For example, the match determination system 100 can receive a user input from a client device defining an edge between nodes of a genealogical data tree. As another example, the match determination system 100 can receive a user input expressly defining a data link or a familial relationship between two individuals or between two data identifiers. As yet another example, the match determination system 100 receives or accesses stored data (e.g., from the database 106) defining data links and/or familial relationships specific to a user account or maintained as ground truth data by the genealogical data system 104.

As additionally illustrated in FIG. 5, the match determination system 100 determines a source data link 506 between the target individual and the source individual. Specifically, the match determination system 100 determines the source data link 506 based on a precursor data match between the precursor entity and the target individual. In at least one embodiment, the match determination system 100 determines the source data link 506 as described above.

As further illustrated in FIG. 5, the match determination system 100 determines (or detects) a data link discrepancy 510 between the additional data link 504 and the source data link 506. In particular, upon determining (or receiving) the data links, the match determination system 100 can perform the act 508 to compare the additional data link 504 and the source data link 506. Based on this comparison, the match determination system 100 can determine (or detect) that there is an actual or probable discrepancy between the two data links. As an example, the match determination system 100 may determine that the additional data link 504 indicates an M5 relationship (e.g., a first cousin once removed relationship) and that the source data link 506 indicates an M4 relationship (e.g., a first cousin relationship). Consequently, the match determination system 100 can determine (or detect) the data link discrepancy 510 between the additional data link 504 and the source data link 506. As another example, the match determination system 100 can determine the data link discrepancy 510 even when the additional data link 504 and the source data link 506 indicate the same meiosis level (e.g., M3). To elaborate, the match determination system 100 can determine a difference or a discrepancy between a half-sibling relationship and a grandparent relationship, where both are types of familial relationship encompassed by an M3 data link.

In one or more embodiments, the match determination system 100 further resolves the data link discrepancy 510. For example, the match determination system 100 automatedly (e.g., independent of user input to perform or carry out) resolves the data link discrepancy 510 by determining a likely data link and/or a likely familial relationship between a source individual and a target individual. Indeed, as described above, the match determination system 100 uses genetic data from a reconstructed data identifier (for a precursor entity) to disambiguate among potential data links and/or potential familial relationships to thereby determine or select a most likely data link or a most likely familial relationship. In some embodiments, the match determination system 100 resolves the data link discrepancy 510 by replacing a discrepant data link (e.g., the additional data link 504) with the source data link 506 derived from the reconstructed data identifier.

Similarly, in one or more embodiments, the match determination system 100 can resolve a discrepancy among familial relationships. For instance, if the data link discrepancy 510 indicates a difference in familial relationship (even within a common meiosis level), the match determination system 100 can replace a discrepant familial relationship (e.g., that of the additional data link 504) with a familial relationship corresponding to the source data link 506.

In one or more embodiments, the match determination system 100 can provide, for display in a graphical user interface (GUI) (e.g., a data link correction interface) of a client device, one or more visual indicators of the data link discrepancy 510. For example, the match determination system 100 may provide a visual indicator that notifies a user or client of the client device that it has determined (or detected) the data link discrepancy 510. In the same or other embodiments, the match determination system 100 may provide one or more selectable elements to correct or remedy the data link discrepancy 510 using (or incorporating) the source data link 506 rather than the additional data link 504. In response to selecting the one or more selectable elements, the match determination system 100 may connect the target individual and the source individual in a data tree (e.g., a family tree). For instance, the match determination system 100 may connect the target individual and the source individual in the data tree based on the source data link 506.

As mentioned above, in the same or other embodiments, the match determination system 100 automates resolution of the data link discrepancy 510. For instance, the match determination system 100 can automatically correct or remedy the data link discrepancy 510 using (or incorporating) the source data link 506 rather than the additional data link 504. Additional GUI details are discussed in greater detail below in relation to FIGS. 6A-6C.

Figure 6A:
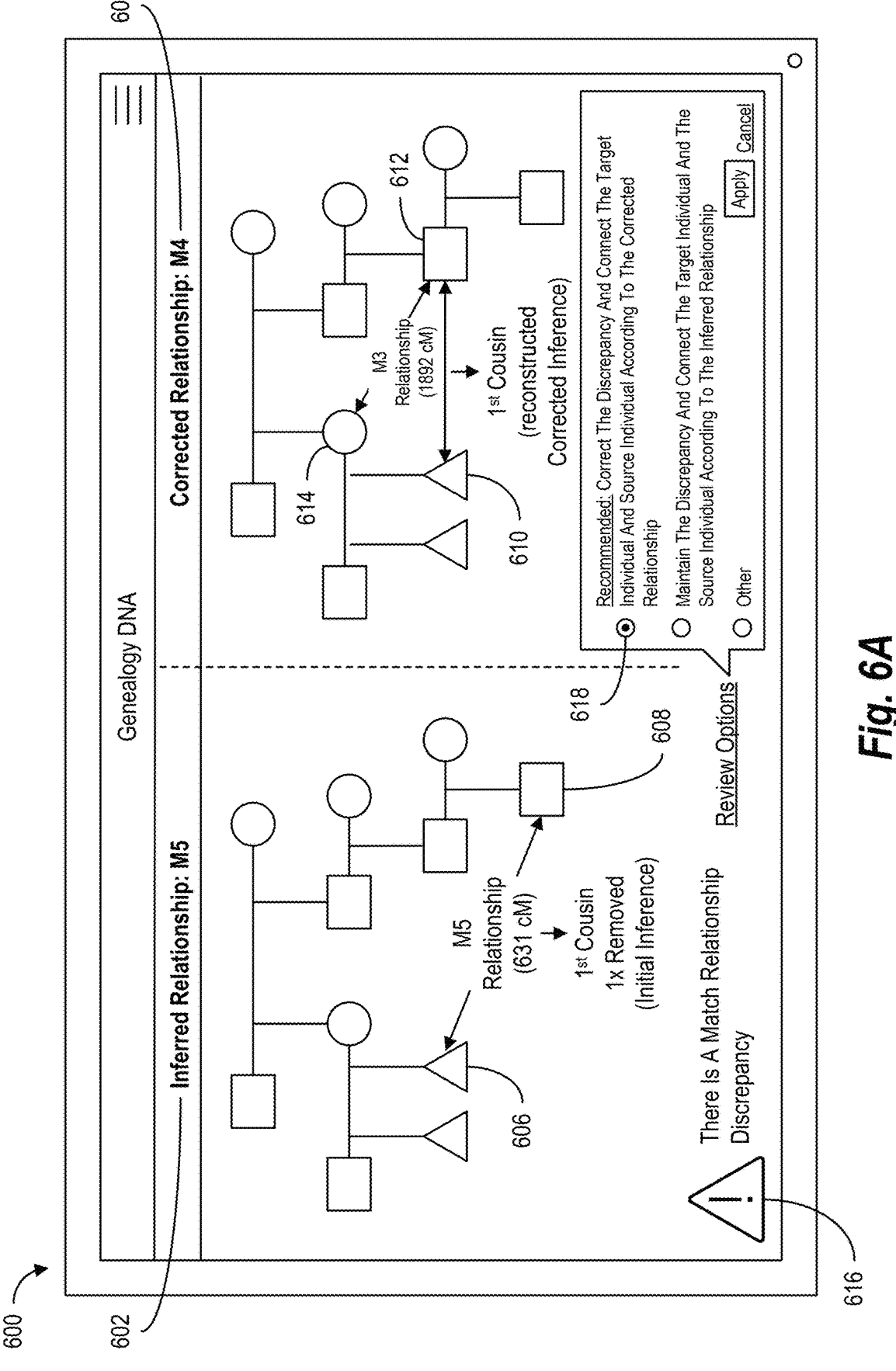
FIGS. 6A-6C illustrate example user interfaces for connecting a target individual and a source individual in a data tree in accordance with one or more embodiments.
Figure 6B:
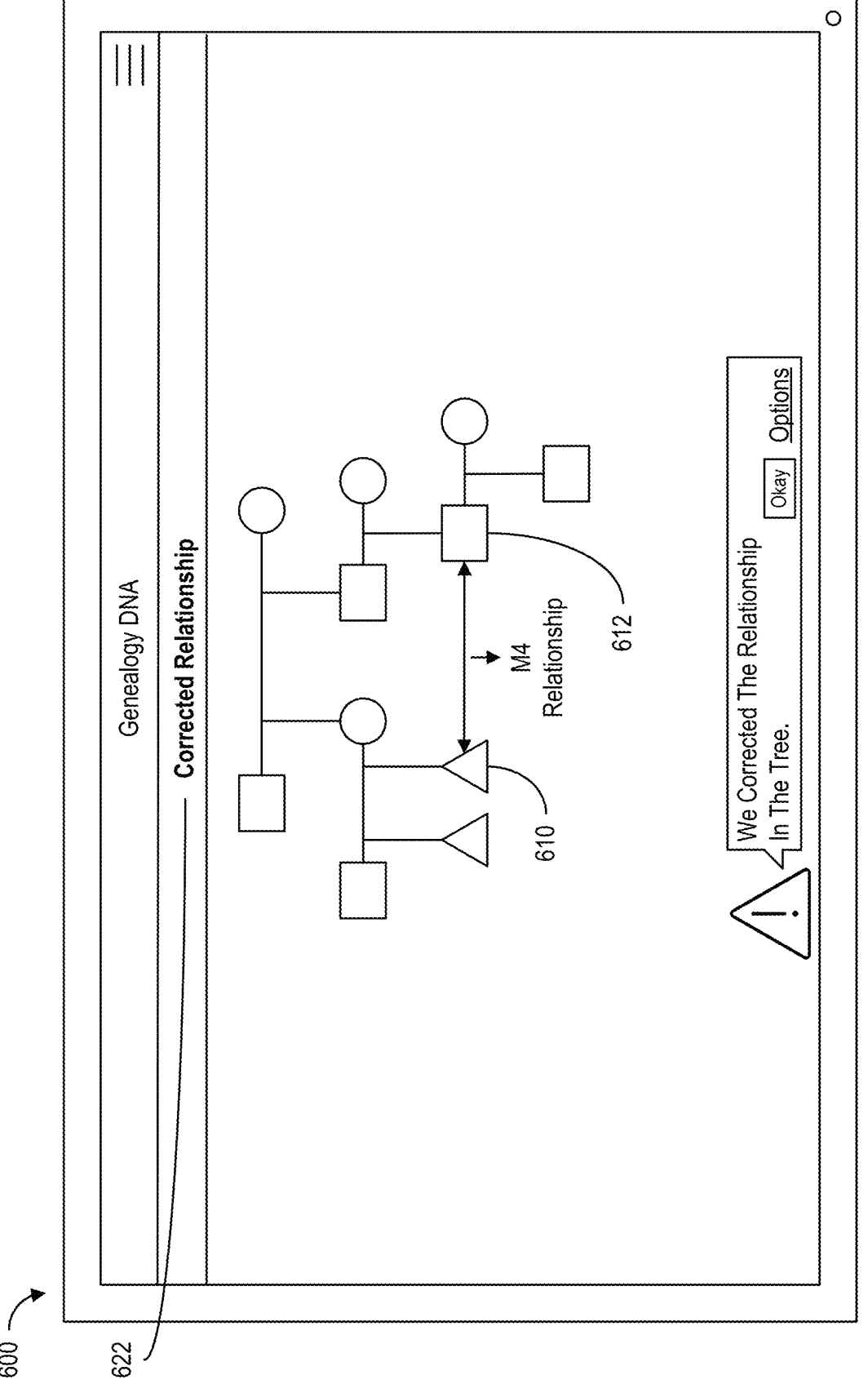
Figure 6C:
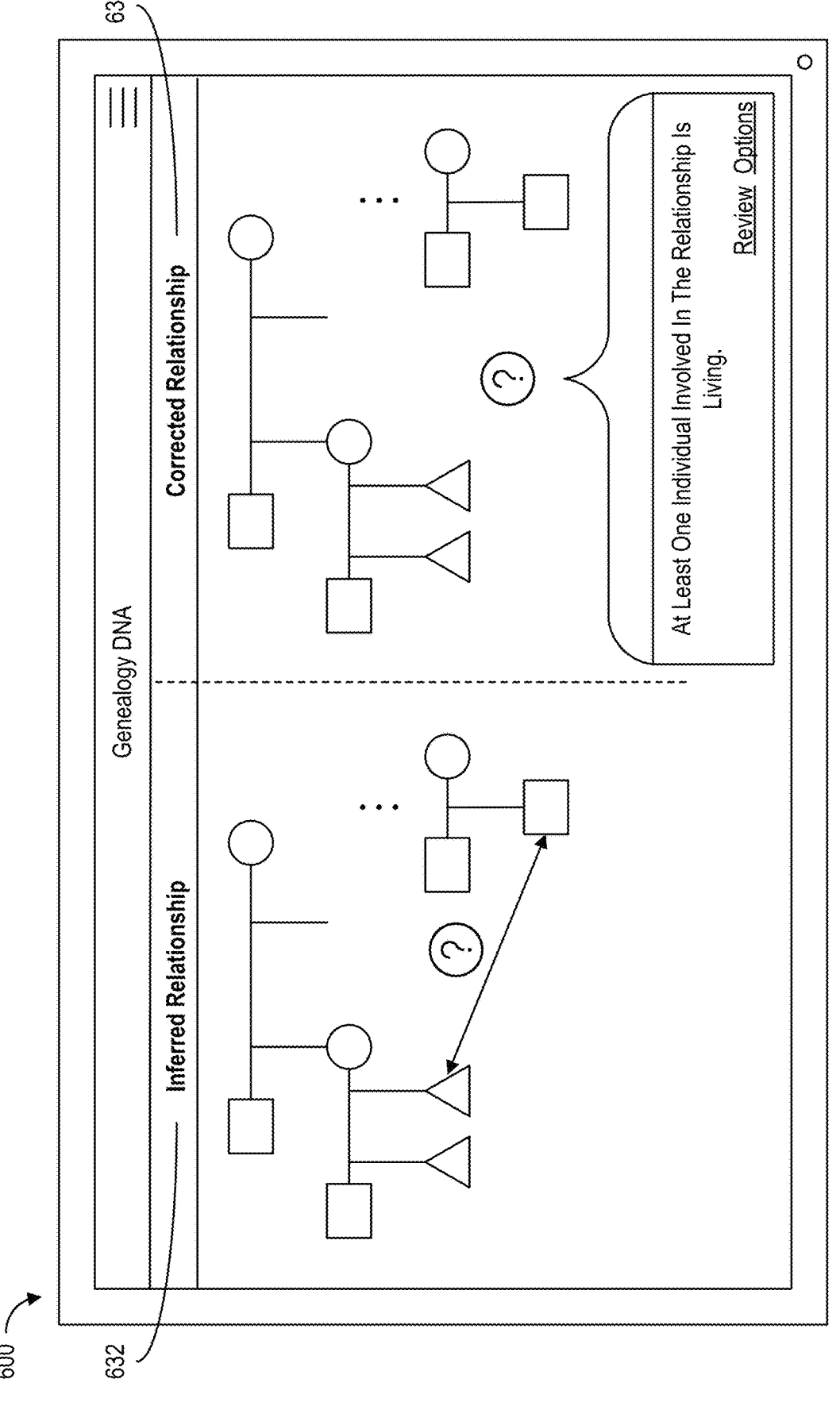

As expressed above, the match determination system 100 can provide, for display in a GUI, one or more visual indicators of a data link discrepancy between a source data link and an additional data link and/or one or more selectable elements to correct or remedy the data link discrepancy. Specifically, in response to detecting a selection of a selectable element, the match determination system 100 may connect a target individual and a source individual in a data tree based on the source data link. FIGS. 6A-6C illustrate example user interfaces for connecting a target individual and a source individual in a data tree in accordance with one or more embodiments.

As illustrated in FIG. 6A, the match determination system 100 generates a graphical user interface (GUI) of the client device for displaying one or more data trees (e.g., one or more family trees) on a client device. Specifically, the match determination system 100 can generate and display a data link correction interface 600 of the client device for connecting individuals or entities together in the one or more data trees. For instance, the match determination system 100 can provide, for display in the data link correction interface 600, a data tree 602 and/or a data tree 604. In one or more embodiments, the match determination system 100 provides the data link correction interface 600 to connect a target individual and a source individual in at least one of the one or more data trees.

As just mentioned, the match determination system 100 can provide, for display in the data link correction interface 600, the data tree 602. In particular, the match determination system 100 can provide the data tree 602 for connecting, in an inferred relationship, a source individual 606 and a target individual 608 based on an additional data link between the source individual 606 and the target individual 608 (as described in greater detail above). For example, as shown in FIG. 6A, the match determination system 100 can infer that the source individual 606 and the target individual 608 have an M5 relationship (or are an M5 match) (e.g., based on determining that both share 631 cM). Further, in some embodiments, the match determination system 100 determines an initial inference of a type of relationship (e.g., an additional data link type) between the source individual 606 and the target individual 608. As an example, the match determination system 100 may provide an initial inference that that the two individuals are first cousins once removed (1$^{st}$ cousins 1× removed).

As mentioned above, the match determination system 100 can provide, for display in the data link correction interface 600, the data tree 604. Specifically, the match determination system 100 can provide the data tree 604 for connecting, in a corrected relationship, a source individual 610 and a target individual 612 based on a source data link between the source individual 610 and the target individual 612 (as described in greater detail above). For instance, as shown in FIG. 6A, the match determination system 100 can determine that the source individual 610 and the target individual 612 have an M4 relationship (or are an M4 match).

To elaborate, by utilizing a reconstructed data identifier for a precursor entity 614, the match determination system 100 can determine a precursor data link between the target individual 612 and the precursor entity 614. For example, the match determination system 100 can determine that that the target individual 612 and the precursor entity 614 have an M3 relationship (or are an M3 match) (e.g., based on determining that both share 1,892 cM). By combining the precursor data link with a data link augmentation (in a process explained in greater detail above), the match determination system 100 can determine the source data link. For example, the match determination system 100 can combine the precursor data link M3 with a determined data link augmentation value of M1 to determine that the source individual 610 and the target individual 612 have an M4 relationship. Further, in some embodiments, the match determination system 100 determines a reconstructed corrected inference of a type of relationship (e.g., a source data link type) between the source individual 610 and the target individual 612. As an example, the match determination system 100 may provide a reconstructed corrected inference that that the two individuals are first cousins.

As also illustrated in FIG. 6A, the match determination system 100 provides one or more visual indicators (e.g., visual indicator 616) of a data link discrepancy. In particular, the match determination system 100 can determine that there is a data link discrepancy between the data tree 602 and the data tree 604 by comparing the additional data link to the source data link (as explained in greater detail above). For example, the match determination system 100 may determine the data link discrepancy by comparing the M5 additional data link to the M4 source data link. In response to determining that there is a data link discrepancy, the match determination system 100 may display the visual indicator 616, indicating that there is a match relationship discrepancy.

As further illustrated in FIG. 6A, the match determination system 100 provides one or more selectable elements (e.g., selectable element 618) to correct the data link discrepancy using the source data link. In particular, in addition to (or alternatively to) providing the one or more visual indicators, the match determination system 100 may provide the one or more selectable elements. For instance, the match determination system 100 may provide the selectable element 618 selectable for correcting the match relationship discrepancy and connect the target individual and the source individual according to the corrected relationship in the data tree 604. In some embodiments, the match determination system 100 may recommend selecting the selectable element 618.

In at least one embodiment, the match determination system 100 provides one or more additional or alternative selectable elements. For example, the match determination system 100 may provide a selectable element that is selectable for maintaining the discrepancy and connecting the target individual and the source individual according to the inferred relationship in the data tree 602. As another example, the match determination system 100 may provide a selectable element that is selectable for providing at least one other option for dealing with the match relationship discrepancy.

As illustrated in FIG. 6B, the match determination system 100 can provide, for display in the data link correction interface 600, a data tree 622 that connects the source individual 610 and the target individual 612. In particular, in response to a selection of at least one of the one or more selectable elements (e.g., the selectable element 618) to correct the data link discrepancy, the match determination system 100 can connect the source individual 610 and the target individual 612 in the data tree 622 based on the source data link. For instance, the match determination system 100 can connect the source individual 610 and the target individual 612 in the data tree 622 according to the corrected relationship of the data tree 604. As an example, the match determination system 100 can connect the source individual 610 and the target individual 612 in the data tree 622 based on the determined M4 relationship (or M4 match).

As also illustrated in FIG. 6B, the match determination system 100 provides, in the data link correction interface 600, at least one digital notification of connecting the source individual 610 and the target individual 612 in the data tree 622 based on the source data link. In some embodiments, upon connecting the source individual 610 and the target individual 612, the match determination system 100 can provide one or more additional or alternative options. For instance, the match determination system 100 may provide an option to undo the connecting the source individual 610 and the target individual 612 in the data tree 622 according to the corrected relationship.

In the same or other embodiments, the match determination system 100 automates resolution of the data link discrepancy. For instance, the match determination system 100 can automatically (e.g., without selection of the one or more selectable elements) correct or remedy the data link discrepancy using (or incorporating) the source data link to replace an additional data link. In some cases, upon automatically correcting or remedying the data link discrepancy, the match determination system 100 provides, in the data link correction interface 600, the at least one digital notification of connecting the source individual 610 and the target individual 612 in the data tree 622 based on the source data link. In some embodiments, upon connecting the source individual 610 and the target individual 612, the match determination system 100 can provide one or more additional or alternative options. For instance, the match determination system 100 may provide an option to undo or remove the edge connecting the source individual 610 and the target individual 612 in the data tree 622 according to the corrected relationship.

As illustrated in FIG. 6C, the match determination system 100 provides, for display in the data link correction interface 600, one or more indeterminate data trees. In particular, when at least one individual involved in a data link and/or data link relationship in a particular data tree is still living, the match determination system 100 may generate and provide an indeterminate data tree. For example, the match determination system 100 may determine that at least one individual in a data tree 632 and/or a data tree 634 is still living. Based on making this determination, the match determination system 100 may withhold providing or displaying all or part of the data tree 632 and/or the data tree 634. For instance, the match determination system 100 may withhold providing a portion of the data tree 632 and/or the data tree 634 that would otherwise depict a data link and/or data link relationship to a living individual who has not given consent to connect him or her in a data tree.

In some embodiments, the match determination system 100 provides one or more options for addressing having a living individual who has not given consent (e.g., for their identity to be viewable by genetic matches or others in the system). As an example, the match determination system 100 may provide one or more options for obtaining proper consent of the living individual to connect him or her in a data tree. In response to addressing this (e.g., by obtaining the proper consent), the match determination system 100 may connect the living individual in a data tree (e.g., the data tree 632 and/or the data tree 634) and provide the data tree for display (e.g., as shown above in FIG. 6A).

Figure 7:
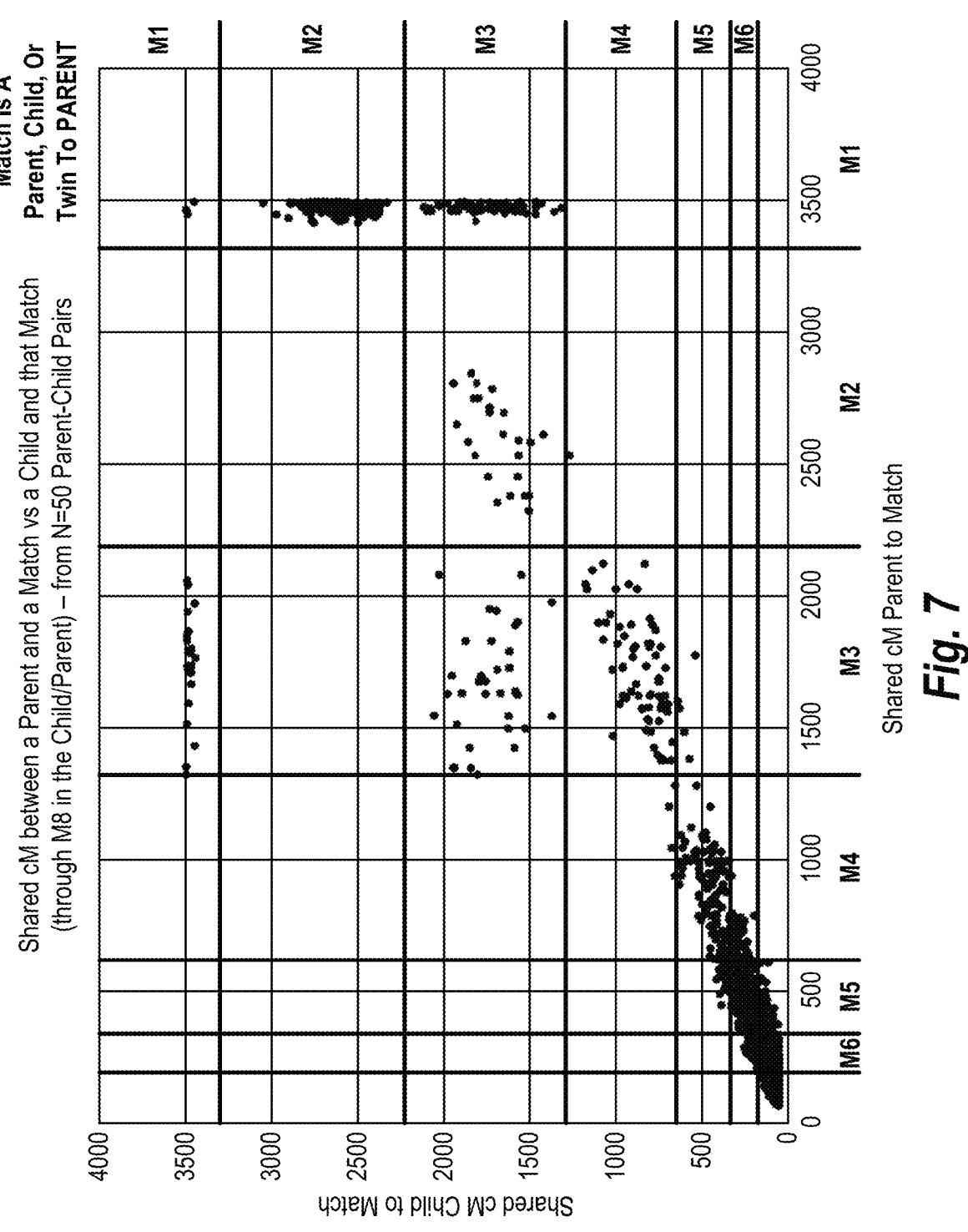
FIG. 7 illustrates an example graph of data link discrepancies between data links in accordance with one or more embodiments.

As expressed above, the match determination system 100 can more accurately determine data links between data identifiers by leveraging reconstructed data identifiers for precursor entities. Specifically, the match determination system 100 reconstructs a data identifier for a precursor entity to more accurately determine a data link and/or to disambiguate potential relationships. FIG. 7 illustrates an example graph of data link discrepancies between data links in accordance with one or more embodiments.

As illustrated in FIG. 7, experimenters have demonstrated on real data that there are data link discrepancies or mismatches between data links. For instance, the experimenters have demonstrated on real data that the number of shared cMs and a predicted data link (e.g., M-level) between (i) a precursor entity (e.g., a parent) to a target individual (e.g., a match) and (ii) a source individual (e.g., a child) to the target individual (e.g., the match) may not agree. As shown in FIG. 7, the x-axis represents the shared cMs between a precursor entity and the target individual, and the y-axis represents the shared cMs between the source individual and the target individual. As also shown in FIG. 7, some data points are misaligned. For instance, some of the data points indicate an M3 data link from the parent to the target individual while also indicating an M3 data link from the source individual (e.g., the child) to the target individual, which is an error (e.g., the data link from the source to the target in this case should be an M4). In one or more embodiments, the match determination system 100 can correct such data link discrepancies or mismatches by relying on the more accurate centimorgans and/or other data (or information) of the precursor entity (e.g., via the reconstructed data identifiers for the precursor entity) and the target individual, as described above.

Indeed, as noted above, the match determination system 100 can utilize a reconstructed data identifier for the precursor entity to more accurately determine a data link between the source individual and the target individual. As described above, the match determination system 100 can utilize the reconstructed data identifier to determine additional genetic data (e.g., IBD segments and/or cM overlap) between a source individual and a target individual, beyond what is determined via a direct comparison between the source individual and the target individual. The match determination system 100 can thus improve information about the heritable characteristics of the source individual's genome, thereby allowing the match determination system 100 to disambiguate a likely data link relationship between the source individual and a target individual from the noise of possible relationships. Accordingly, as shown in FIG. 7, the match determination system 100 can resolve discrepant M3 data links from the source individual (e.g., the child) to the target individual (e.g., the match) by replacing them with M4 data links as derived from the reconstructed data identifier of the precursor entity (e.g., the parent).

Figure 8:
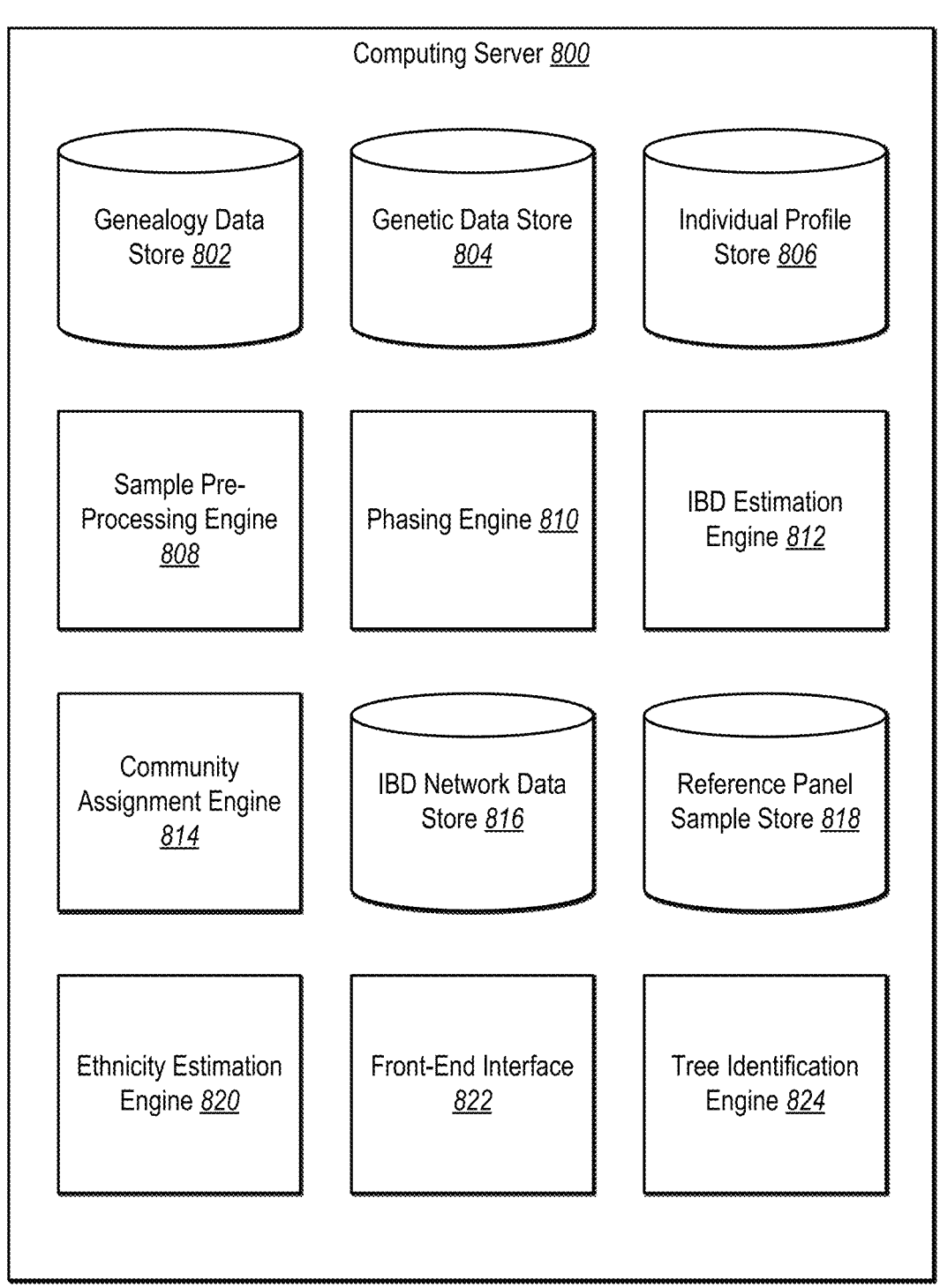
FIG. 8 illustrates an example block diagram of an architecture of an example computing server in accordance with one or more embodiments.

FIG. 8 is a block diagram of an architecture of an example computing server 800 (e.g., the server(s) 102), in accordance with some embodiments. In the embodiment shown in FIG. 8, the computing server 800 includes a genealogy data store 802, a genetic data store 804, an individual profile store 806, a sample pre-processing engine 808, a phasing engine 810, an identity by descent (IBD) estimation engine 812, a community assignment engine 814, an IBD network data store 816, a reference panel sample store 818, an ethnicity estimation engine 820, a front-end interface 822, and a tree management engine 824. The functions of the computing server 800 may be distributed among the elements in a different manner than described. In various embodiments, the computing server 800 may include different components and fewer or additional components. Each of the various data stores may be a single storage device, a server controlling multiple storage devices, or a distributed network that is accessible through multiple nodes (e.g., a cloud storage system).

The computing server 800 stores various data of different individuals, including genetic data, genealogy data, and survey response data. The computing server 800 processes the genetic data of individuals (e.g., genetic profiles) to identify shared identity-by-descent (IBD) segments between individuals. The genealogy data and survey response data may be part of user account profile data. The amount and type of user account profile data stored for each individual may vary based on the information of an individual, which determined or received from the individual through creating an account and profile at a system (e.g., the genealogical data system 104) operated by the computing server 800, and through updating the profile, family tree, and social network at the system, in some cases linking a profile with genetic data. The computing server 800 may also include answers to survey questions regarding various traits of individuals, such as phenotypes, characteristics, preferences, habits, lifestyle, and environment for user accounts.

The genealogy data store 802 may store genealogy data, including various types of data that are related to tracing family relatives of individuals. Examples of genealogy data include names (first, last, middle, suffixes), gender, birth locations, date of birth, date of death, marriage information, spouse's information kinships, family history, dates and places for life events (e.g., birth and death), other vital data, and the like. In some instances, family history can take the form of a pedigree of an individual (e.g., the recorded relationships in the family). The family tree information associated with an individual may include one or more specified nodes. Each node in the family tree represents the individual, an ancestor of the individual who might have passed down genetic material to the individual, and the individual's other relatives including siblings, cousins, and offspring in some cases. Genealogy data may also include connections and relationships among user accounts of the computing server 800.

In addition to user account data, genealogy data may also take other forms that are obtained from various sources such as public records and third-party data collectors. For example, genealogical records from public sources include birth records, marriage records, death records, census records, court records, probate records, adoption records, and/or obituary records. Likewise, genealogy data may include data from one or more family trees of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, and/or a motor vehicle database.

Furthermore, the genealogy data store 802 may also include relationship information inferred from the genetic data stored in the genetic data store 804 and information received from the individuals. For example, the relationship information may indicate which individuals are genetically related, how they are related, how many generations back they share common ancestors, lengths and locations of IBD segments shared, which genetic communities an individual is a part of, variants carried by the individual, and the like.

The computing server 800 maintains genetic datasets of individuals in the genetic data store 804. A genetic dataset of an individual may be a digital dataset of nucleotide data (e.g., SNP data) and corresponding metadata. A genetic dataset may contain data on the whole or portions of an individual's genome. The genetic data store 804 may store a pointer to a location associated with the genealogy data store 802 associated with the individual. A genetic dataset may take different forms. In some embodiments, a genetic dataset may take the form of a base pair sequence of the sequencing result of an individual. A base pair sequence dataset may include the whole genome of the individual (e.g., obtained from a whole-genome sequencing) or some parts of the genome (e.g., genetic loci of interest).

In another embodiment, a genetic dataset may take the form of sequences of genetic markers. Examples of genetic markers may include target SNP loci (e.g., allele sites) filtered from the sequencing results. A SNP locus that is single base pair long may also be referred to a SNP site. A SNP locus may be associated with a unique identifier. The genetic dataset may be in a form of diploid data that includes a sequencing of genotypes, such as genotypes at the target SNP loci, or the whole base pair sequence that includes genotypes at known SNP loci and other base pair sites that are not commonly associated with known SNPs. The diploid dataset may be referred to as a genotype dataset or a genotype sequence. Genotype may have a different meaning in various contexts. In one context, an individual's genotype may refer to a collection of diploid alleles of an individual. In other contexts, a genotype may be a pair of alleles present on two chromosomes for an individual at a given genetic marker such as a SNP site.

Genotype data for a SNP site may include a pair of alleles. The pair of alleles may be homozygous (e.g., A-A or G-G) or heterozygous (e.g., A-T, C-T). Instead of storing the actual nucleotides, the genetic data store 804 may store genetic data that are converted to bits. For a given SNP site, oftentimes only two nucleotide alleles (instead of all 4) are observed. As such, a 2-bit number may represent a SNP site. For example, 00 may represent homozygous first alleles, 11 may represent homozygous second alleles, and 01 or 10 may represent heterozygous alleles. A separate library may store what nucleotide corresponds to the first allele and what nucleotide corresponds to the second allele at a given SNP site.

A diploid dataset may also be phased into two sets of haploid data, one corresponding to a first parent side and another corresponding to a second parent side. The phased datasets may be referred to as haplotype datasets or haplotype sequences. Similar to genotype, haplotype may have a different meaning in various contexts. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

The individual profile store 806 stores profiles and related metadata associated with various individuals appeared in the computing server 800. A computing server 800 may use unique individual identifiers to identify various user accounts and other non-user accounts that might appear in other data sources such as ancestors or historical persons who appear in any family tree or genealogy database. A unique individual identifier may be a hash of certain identification information of an individual, such as a user account's account name, user account's name, date of birth, location of birth, or any suitable combination of the information. The profile data related to an individual may be stored as metadata associated with an individual's profile. For example, the unique individual identifier and the metadata may be stored as a key-value pair using the unique individual identifier as a key.

An individual's profile data may include various kinds of information related to the individual. The metadata about the individual may include one or more pointers associating genetic datasets such as genotype and phased haplotype data of the individual that are saved in the genetic data store 804. The metadata about the individual may also be individual information related to family trees and pedigree datasets that include the individual. The profile data may further include declarative information about the user account that was authorized by the user account to be shared and may also include information inferred by the computing server 800. Other examples of information stored in a user account profile may include biographic, demographic, and other types of descriptive information such as work experience, educational history, gender, hobbies, or preferences, and/or location. In some embodiments, the user account profile data may also include one or more photos of the user accounts and photos of relatives (e.g., ancestors) of the user accounts that are uploaded by the user accounts. A user account may authorize the computing server 800 to analyze one or more photos to extract information, such as the user account's or relative's appearance traits (e.g., blue eyes, curved hair, etc.), from the photos. The appearance traits and other information extracted from the photos may also be saved in the profile store. In some cases, the computing server may allow user accounts to upload many different photos of the user accounts, their relatives, and even friends. User account profile data may also be obtained from other suitable sources, including historical records (e.g., records related to an ancestor), medical records, military records, photographs, other records indicating one or more traits, and other recorded data.

For example, the computing server 800 may present various survey questions to its user accounts from time to time. The responses to the survey questions may be stored at individual profile store 806. The survey questions may be related to various aspects of the user accounts and the user account families. Some survey questions may be related to user account phenotypes, while other questions may be related to environmental factors of the user accounts.

Survey questions may concern health or disease-related phenotypes, such as questions related to the presence or absence of genetic diseases or disorders, inheritable diseases or disorders, or other common diseases or disorders that have a family history as one of the risk factors, questions regarding any diagnosis of increased risk of any diseases or disorders, and questions concerning wellness-related issues such as a family history of obesity, and/or family history of causes of death. The diseases identified by the survey questions may be related to single-gene diseases or disorders that are caused by a single-nucleotide variant, an insertion, or a deletion. The diseases identified by the survey questions may also be multifactorial inheritance disorders that may be caused by a combination of environmental factors and genes. Examples of multifactorial inheritance disorders may include heart disease, Alzheimer's disease, diabetes, cancer, and obesity. The computing server 800 may obtain data on a user account's disease-related phenotypes from survey questions about the health history of the user account and her family and also from health records uploaded by the user account.

Survey questions also may be related to other types of phenotypes such as appearance traits of the user accounts. A survey regarding appearance traits and characteristics may include questions related to eye color, iris pattern, freckles, chin types, finger length, dimple chin, earlobe types, hair color, hair curl, skin pigmentation, susceptibility to skin burn, bitter taste, male baldness, baldness pattern, presence of unibrow, presence of wisdom teeth, height, and weight. A survey regarding other traits also may include questions related to user account taste and smell such as the ability to taste bitterness, asparagus smell, and/or cilantro aversion. A survey regarding traits may further include questions related to user account body conditions such as lactose tolerance, caffeine consumption, malaria resistance, norovirus resistance, muscle performance, alcohol flush, etc. Other survey questions regarding a person's physiological or psychological traits may include vitamin traits and sensory traits such as the ability to sense an asparagus metabolite. Traits may also be collected from historical records, electronic health records and electronic medical records.

The computing server 800 also may present various survey questions related to the environmental factors of user accounts. In this context, an environmental factor may be a factor that is not directly connected to the genetics of user accounts. Environmental factors may include user account preferences, habits, and lifestyles. For example, a survey regarding user account preferences may include questions related to things and activities that user accounts like or dislike, such as types of music a user account enjoys, dancing preference, party-going preference, certain sports that a user account plays, video game preferences, etc. Other questions may be related to diet preferences such as liking or disliking a certain type of food (e.g., ice cream, egg). A survey4 related to habits and lifestyle may include questions regarding smoking habits, alcohol consumption and frequency, daily exercise duration, sleeping habits (e.g., morning person versus night person), sleeping cycles and problems, hobbies, and travel preferences. Additional environmental factors may include diet amount (calories, macronutrients), physical fitness abilities (e.g., stretching, flexibility, heart rate recovery), family type (adopted family or not, has siblings or not, lived with extended family during childhood), property and item ownership (has home or rents, has a smartphone or does not, has a car or does not).

Surveys also may be related to other environmental factors such as geographical, social-economic, or cultural factors. Geographical questions may include questions related to the birth location, family migration history, town, or city of current or past residence. Social-economic questions may be related to education level, income, occupations, and/or self-identified demographic groups. Questions related to culture may concern native language, language spoken at home, customs, and/or dietary practices. Other questions related to cultural and behavioral questions are also possible.

For any survey questions asked, the computing server 800 may also ask an individual the same or similar questions regarding the traits and environmental factors of the ancestors, family members, other relatives or friends of the individual. For example, the computing server 800 may ask about the native language of the user account and the native languages of parents and grandparents. The computing server 800 may also ask about the health history of family members.

In addition to storing the survey data in the individual profile store 806, the computing server 800 may store some responses that correspond to data related to genealogical and genetics respectively to genealogy data store 802 and genetic data store 804.

The user account profile data, photos of user accounts, survey response data, the genetic data, and the genealogy data may be subject to the privacy and authorization setting of the user accounts to specify any data related to the user accounts that can be accessed, stored, obtained, or otherwise used. For example, when presented with a survey question, a user account may select to answer or skip the question. The computing server 800 may present user accounts from time to time information regarding user accounts' selection of the extent of information and data shared. The computing server 800 also may maintain and enforce one or more privacy settings for user accounts in connection with the access of the user account profile data, photos, genetic data, and other sensitive data. For example, the user account may pre-authorize the access to the data and may change the setting as wished. The privacy settings also may allow a user account to specify (e.g., by opting out, by not opting in) whether the computing server 800 may receive, collect, log, or store particular data associated with the user account for any purpose. A user account may restrict her data at various levels. For example, on one level, the data may not be accessed by the computing server 800 for purposes other than displaying the data in the user account's own profile. On another level, the user account may authorize anonymization of her data and participate in studies and research conducted by the computing server 800 such as a large-scale genetic study. On yet another level, the user account may turn some portions of her genealogy data public to allow the user account to be discovered by other user accounts (e.g., potential relatives) and be connected to one or more family trees. Access or sharing of any information or data in the computing server 800 may also be subject to one or more similar privacy policies. Data and content objects in the computing server 800 may also be associated with different levels of restriction. The computing server 800 may also provide various notification features to inform and remind user accounts of their privacy and access settings. For example, when privacy settings for a data entry allow a particular user account or other entities to access the data, the data may be described as being "visible," "public," or other suitable labels, contrary to a "private" label.

In some cases, the computing server 800 may have a heightened privacy protection on certain types of data and data related to certain vulnerable groups. In some cases, the heightened privacy settings may strictly prohibit the use, analysis, and sharing of data related to a certain vulnerable group. In other cases, the heightened privacy settings may specify that data subject to those settings require prior approval for access, publication, or other use. In some cases, the computing server 800 may provide the heightened privacy as a default setting for certain types of data, such as genetic data or any data that the user account marks as sensitive. The user account may opt in to sharing of those data or change the default privacy settings. In other cases, the heightened privacy settings may apply across the board for all data of certain groups of user accounts. For example, if computing server 800 determines that the user account is a minor or has recognized that a picture of a minor is uploaded, the computing server 800 may designate all profile data associated with the minor as sensitive. In those cases, the computing server 800 may have one or more extra steps in seeking and confirming any sharing or use of the sensitive data.

The sample pre-processing engine 808 receives and pre-processes data received from various sources to change the data into a format used by the computing server 800. For genealogy data, the sample pre-processing engine 808 may receive data from an individual. To collect the user account data (e.g., genealogical and survey data), the computing server 800 may cause an interactive user account interface on a client device to display interface elements in which user accounts can provide genealogy data and survey data. Additional data may be obtained from scans of public records. The data may be manually provided or automatically extracted via, for example, optical character recognition (OCR) performed on census records, town or government records, or any other item of printed or online material. Some records may be obtained by digitalizing written records such as older census records, birth certificates, and/or death certificates.

The sample pre-processing engine 808 may also receive raw data from a genetic data extraction service server. A genetic data extraction service server may perform laboratory analysis of biological samples of user accounts and generate sequencing results in the form of digital data. The sample pre-processing engine 808 may receive the raw genetic datasets from the genetic data extraction service server. Most of the mutations that are passed down to descendants are related to single-nucleotide polymorphism (SNP). SNP is a substitution of a single nucleotide that occurs at a specific position in the genome. The sample pre-processing engine 808 may convert the raw base pair sequence into a sequence of genotypes of target SNP sites. Alternatively, the pre-processing of this conversion may be performed by the genetic data extraction service server. The sample pre-processing engine 808 identifies autosomal SNPs in an individual's genetic dataset. In some embodiments, the SNPs may be autosomal SNPs. In some embodiments, 800,000 SNPs may be identified in an individual's data and may be stored in genetic data store 804. Alternatively, in some embodiments, a genetic dataset may include at least 10,000 SNP sites. In another embodiment, a genetic dataset may include at least 100,000 SNP sites. In yet another embodiment, a genetic dataset may include at least 300,000 SNP sites. In yet another embodiment, a genetic dataset may include at least 1,000,000 SNP sites. The sample pre-processing engine 808 may also convert the nucleotides into bits. The identified SNPs, in bits or in other suitable formats, may be provided to the phasing engine 810 which phases the individual's diploid genotypes to generate a pair of haplotypes for each user account.

The phasing engine 810 phases diploid genetic dataset into a pair of haploid genetic datasets and may perform imputation of SNP values at certain sites whose alleles are missing. An individual's haplotype may refer to a collection of alleles (e.g., a sequence of alleles) that are inherited from a parent.

Phasing may include a process of determining the assignment of alleles (particularly heterozygous alleles) to chromosomes. Owing to sequencing conditions and other constraints, a sequencing result often includes data regarding a pair of alleles at a given SNP locus of a pair of chromosomes but may not be able to distinguish which allele belongs to which specific chromosome. The phasing engine 810 uses a genotype phasing algorithm to assign one allele to a first chromosome and another allele to another chromosome. The genotype phasing algorithm may be developed based on an assumption of linkage disequilibrium (LD), which states that haplotype in the form of a sequence of alleles tends to cluster together. The phasing engine 810 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as a training sample because the correct phasing of the child is almost certain by comparing the child's genotypes to the parent's genetic datasets. The haplotype-cluster model may be generated iteratively along with the phasing process with a large number of unphased genotype datasets. The haplotype-cluster model may also be used to impute one or more missing data.

By way of example, the phasing engine 810 may use a directed acyclic graph model such as a hidden Markov model (HMM) to perform the phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing engine 810 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. Pat. No. 10,679,729, entitled "Haplotype Phasing Models," granted on Jun. 9, 2020, describes example embodiments of haplotype phasing. Other example phasing embodiments are described in U.S. Patent Application Publication No. US 2021/0034647, entitled "Clustering of Matched Segments to Determine Linkage of Dataset in a Database," published on Feb. 4, 2021.

The IBD estimation engine 812 estimates the amount of shared genetic segments between a pair of individuals based on phased genotype data (e.g., haplotype datasets) that are stored in the genetic data store 804. IBD segments may be segments identified in a pair of individuals that are putatively determined to be inherited from a common ancestor. The IBD estimation engine 812 retrieves a pair of haplotype datasets for each individual. The IBD estimation engine 812 may divide each haplotype dataset sequence into a plurality of windows. Each window may include a fixed number of SNP sites (e.g., about 100 SNP sites). The IBD estimation engine 812 identifies one or more seed windows in which the alleles at all SNP sites in at least one of the phased haplotypes between two individuals are identical. The IBD estimation engine 812 may expand the match from the seed windows to nearby windows until the matched windows reach the end of a chromosome or until a homozygous mismatch is found, which indicates the mismatch is not attributable to potential errors in phasing or imputation. The IBD estimation engine 812 determines the total length of matched segments, which may also be referred to as IBD segments. The length may be measured in the genetic distance in the unit of centimorgans (cM). A unit of centimorgan may be a genetic length. For example, two genomic positions that are one cM apart may have a 1% chance during each meiosis of experiencing a recombination event between the two positions. The computing server 800 may save data regarding individual pairs who share a length of IBD segments exceeding a predetermined threshold (e.g., 6 cM), in a suitable data store such as in the genealogy data store 802. U.S. Pat. No. 10,114,922, entitled "Identifying Ancestral Relationships Using a Continuous stream of Input," granted on Oct. 30, 2018, and U.S. Pat. No. 10,720, 229, entitled "Reducing Error in Predicted Genetic Relationships," granted on Jul. 21, 2020, describe example embodiments of IBD estimation.

Typically, individuals who are closely related share a relatively large number of IBD segments, and the IBD segments tend to have longer lengths (individually or in aggregate across one or more chromosomes). In contrast, individuals who are more distantly related share relatively fewer IBD segments, and these segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity. For example, the IBD affinity may be measured in terms of the length of IBD segments shared between two individuals.

Community assignment engine 814 assigns individuals to one or more genetic communities based on the genetic data of the individuals. A genetic community may correspond to an ethnic origin or a group of people descended from a common ancestor. The granularity of genetic community classification may vary depending on embodiments and methods used to assign communities. For example, in some embodiments, the communities may be African, Asian, European, etc. In another embodiment, the European community may be divided into Irish, German, Swedes, etc. In yet another embodiment, the Irish may be further divided into Irish in Ireland, Irish immigrated to America in 1800, Irish immigrated to America in 1802, etc. The community classification may also depend on whether a population is admixed or unadmixed. For an admixed population, the classification may further be divided based on different ethnic origins in a geographical region.

Community assignment engine 814 may assign individuals to one or more genetic communities based on their genetic datasets using machine learning models trained by unsupervised learning or supervised learning. In an unsupervised approach, the community assignment engine 814 may generate data representing a partially connected undirected graph. In this approach, the community assignment engine 814 represents individuals as nodes. Some nodes are connected by edges whose weights are based on IBD affinity between two individuals represented by the nodes. For example, if the total length of two individuals' shared IBD segments does not exceed a predetermined threshold, the nodes are not connected. The edges connecting two nodes are associated with weights that are measured based on the IBD affinities. The undirected graph may be referred to as an IBD network. The community assignment engine 814 uses clustering techniques such as modularity measurement (e.g., the Louvain method) to classify nodes into different clusters in the IBD network. Each cluster may represent a community. The community assignment engine 814 may also determine sub-clusters, which represent sub-communities. The computing server 800 saves the data representing the IBD network and clusters in the IBD network data store 816. U.S. Pat. No. 10,223,498, entitled "Discovering Population Structure from Patterns of Identity-By-Descent," granted on Mar. 5, 2019, describes example embodiments of community detection and assignment.

The community assignment engine 814 may also assign communities using supervised techniques. For example, genetic datasets of known genetic communities (e.g., individuals with confirmed ethnic origins) may be used as training sets that have labels of the genetic communities. Supervised machine learning classifiers, such as logistic regressions, support vector machines, random forest classifiers, and neural networks may be trained using the training set with labels. A trained classifier may distinguish binary or multiple classes. For example, a binary classifier may be trained for each community of interest to determine whether a target individual's genetic dataset belongs or does not belong to the community of interest. A multi-class classifier such as a neural network may also be trained to determine whether the target individual's genetic dataset most likely belongs to one of several possible genetic communities.

Reference panel sample store 818 stores reference panel samples for different genetic communities. A reference panel sample is a genetic data of an individual whose genetic data is the most representative of a genetic community. The genetic data of individuals with the typical alleles of a genetic community may serve as reference panel samples. For example, some alleles of genes may be over-represented (e.g., being highly common) in a genetic community. Some genetic datasets include alleles that are commonly present among members of the community. Reference panel samples may be used to train various machine learning models in classifying whether a target genetic dataset belongs to a community, determining the ethnic composition of an individual, and determining the accuracy of any genetic data analysis, such as by computing a posterior probability of a classification result from a classifier.

A reference panel sample may be identified in different ways. In some embodiments, an unsupervised approach in community detection may apply the clustering algorithm recursively for each identified cluster until the sub-clusters contain a number of nodes that are smaller than a threshold (e.g., contains fewer than 1000 nodes). For example, the community assignment engine 814 may construct a full IBD network that includes a set of individuals represented by nodes and generate communities using clustering techniques. The community assignment engine 814 may randomly sample a subset of nodes to generate a sampled IBD network. The community assignment engine 814 may recursively apply clustering techniques to generate communities in the sampled IBD network. The sampling and clustering may be repeated for different randomly generated sampled IBD networks for various runs. Nodes that are consistently assigned to the same genetic community when sampled in various runs may be classified as a reference panel sample. The community assignment engine 814 may measure the consistency in terms of a predetermined threshold. For example, if a node is classified to the same community 95% (or another suitable threshold) of the times whenever the node is sampled, the genetic dataset corresponding to the individual represented by the node may be regarded as a reference panel sample. Additionally, or alternatively, the community assignment engine 814 may select N most consistently assigned nodes as a reference panel for the community.

Other ways to generate reference panel samples are also possible. For example, the computing server 800 may collect a set of samples and gradually filter and refine the samples until high-quality reference panel samples are selected. For example, a candidate reference panel sample may be selected from an individual whose recent ancestors are born at a certain birthplace. The computing server 800 may also draw sequence data from the Human Genome Diversity Project (HGDP). Various candidates may be manually screened based on their family trees, relatives' birth location, and other quality control. Principal component analysis may be used to create clusters of genetic data of the candidates. Each cluster may represent an ethnicity. The predictions of the ethnicity of those candidates may be compared to the ethnicity information provided by the candidates to perform further screening.

The ethnicity estimation engine 820 estimates the ethnicity composition of a genetic dataset of a target individual. The genetic datasets used by the ethnicity estimation engine 820 may be genotype datasets or haplotype datasets. For example, the ethnicity estimation engine 820 estimates the ancestral origins (e.g., ethnicity) based on the individual's genotypes or haplotypes at the SNP sites. To take a simple example of three ancestral populations corresponding to African, European and Native American, an admixed user account may have nonzero estimated ethnicity proportions for all three ancestral populations, with an estimate such as [0.05, 0.65, 0.30], indicating that the user account's genome is 5% attributable to African ancestry, 65% attributable to European ancestry and 30% attributable to Native American ancestry. The ethnicity estimation engine 820 generates the ethnic composition estimate and stores the estimated ethnicities in a data store of computing server 800 with a pointer in association with a particular user account.

In some embodiments, the ethnicity estimation engine 820 divides a target genetic dataset into a plurality of windows (e.g., about 1000 windows). Each window includes a small number of SNPs (e.g., 300 SNPs). The ethnicity estimation engine 820 may use a directed acyclic graph model to determine the ethnic composition of the target genetic dataset. The directed acyclic graph may represent a trellis of an inter-window hidden Markov model (HMM). The graph includes a sequence of a plurality of node groups. Each node group, representing a window, includes a plurality of nodes. The nodes represent different possibilities of labels of genetic communities (e.g., ethnicities) for the window. A node may be labeled with one or more ethnic labels. For example, a level includes a first node with a first label representing the likelihood that the window of SNP sites belongs to a first ethnicity and a second node with a second label representing the likelihood that the window of SNPs belongs to a second ethnicity. Each level includes multiple nodes so that there are many possible paths to traverse the directed acyclic graph.

The nodes and edges in the directed acyclic graph may be associated with different emission probabilities and transition probabilities. An emission probability associated with a node represents the likelihood that the window belongs to the ethnicity labeling the node given the observation of SNPs in the window. The ethnicity estimation engine 820 determines the emission probabilities by comparing SNPs in the window corresponding to the target genetic dataset to corresponding SNPs in the windows in various reference panel samples of different genetic communities stored in the reference panel sample store 818. The transition probability between two nodes represents the likelihood of transition from one node to another across two levels. The ethnicity estimation engine 820 determines a statistically likely path, such as the most probable path or a probable path that is at least more likely than 95% of other possible paths, based on the transition probabilities and the emission probabilities. A suitable dynamic programming algorithm such as the Viterbi algorithm or the forward-backward algorithm may be used to determine the path. After the path is determined, the ethnicity estimation engine 820 determines the ethnic composition of the target genetic dataset by determining the label compositions of the nodes that are included in the determined path. U.S. Pat. No. 10,558,930, entitled "Local Genetic Ethnicity Determination System," granted on Feb. 11, 2020 and U.S. Pat. No. 10,692,587, granted on Jun. 23, 2020, entitled "Global Ancestry Determination System" describe different example embodiments of ethnicity estimation.

The front-end interface 822 displays various results determined by the computing server 800. The results and data may include the IBD affinity between a user account and another individual, the community assignment of the user account, the ethnicity estimation of the user account, phenotype prediction and evaluation, genealogy data search, family tree and pedigree, relative profile and other information. The front-end interface 822 may allow user accounts to manage their profile and data trees (e.g., family trees). The user accounts may view various public family trees stored in the computing server 800 and search for individuals and their genealogy data via the front-end interface 822. The computing server 800 may suggest or allow the user account to manually review and select potentially related individuals (e.g., relatives, ancestors, close family members) to add to the user account's data tree. The front-end interface 822 may be a graphical user account interface (GUI) that displays various information and graphical elements. The front-end interface 822 may take different forms. In one case, the front-end interface 822 may be a software application that can be displayed on an electronic device such as a computer or a smartphone. The software application may be developed by the entity controlling the computing server 800 and be downloaded and installed on the client device 108. In another case, the front-end interface 822 may take the form of a webpage interface of the computing server 800 that allows user accounts to access their family tree and genetic analysis results through web browsers. In yet another case, the front-end interface 822 may provide an application program interface (API).

The tree management engine 824 performs computations and other processes related to user accounts' management of their data trees such as family trees. The tree management engine 824 may allow a user account to build a data tree from scratch or to link the user account to existing data trees. In some embodiments, the tree management engine 824 may suggest a connection between a target individual and a family tree that exists in the family tree database by identifying potential family trees for the target individual and identifying one or more most probable positions in a potential family tree. A user account (target individual) may wish to identify family trees to which he or she may potentially belong. Linking a user account to a family tree or building a family may be performed automatically, manually, or using techniques with a combination of both. In an embodiment of an automatic tree matching, the tree management engine 824 may receive a genetic dataset from the target individual as input and search related individuals that are IBO-related to the target individual. The tree management engine 824 may identify common ancestors. Each common ancestor may be common to the target individual and one of the related individuals. The tree management engine 824 may in turn output potential family trees to which the target individual may belong by retrieving family trees that include a common ancestor and an individual who is IBO-related to the target individual. The tree management engine 824 may further identify one or more probable positions in one of the potential family trees based on information associated with matched genetic data between the target individual and DNA test takers in the potential family trees through one or more machine learning models or other heuristic algorithms. For example, the tree management engine 824 may try putting the target individual in various possible locations in the family tree and determine the highest probability position(s) based on the genetic datasets of the target individual and other DNA test takers in the family tree and based on genealogy data available to the tree management engine 824. The tree management engine 824 may provide one or more family trees from which the target individual may select. For a suggested family tree, the tree management engine 824 may also provide information on how the target individual is related to other individuals in the tree. In a manual tree building, a user account may browse through public family trees and public individual entries in the genealogy data store 802 and individual profile store 806 to look for potential relatives that can be added to the user account's family tree. The tree management engine 824 may automatically search, rank, and suggest individuals for the user account conduct manual reviews as the user account makes progress in the front-end interface 822 in building the family tree.

As used herein, "pedigree" and "family tree" may be interchangeable and may refer to a family tree chart or pedigree chart that shows, diagrammatically, family information, such as family history information, including parentage, offspring, spouses, siblings, or otherwise for any suitable number of generations and/or people, and/or data pertaining to persons represented in the chart. U.S. Pat. No. 11,429,615, entitled "Linking Individual Datasets to a Database," granted on Aug. 30, 2022, describes example embodiments of how an individual may be linked to existing family trees.

The components of the match determination system 100 can include software, hardware, or both. For example, the components of the match determination system 100 can include one or more instructions stored on a computer-readable storage medium and executable by processors of one or more computing devices. When executed by one or more processors, the computer-executable instructions of the match determination system 100 can cause a computing device to perform the methods described herein. Alternatively, the components of the match determination system 100 can comprise hardware, such as a special purpose processing device to perform a certain function or group of functions. Additionally or alternatively, the components of the match determination system 100 can include a combination of computer-executable instructions and hardware.

Furthermore, the components of the match determination system 100 performing the functions described herein may, for example, be implemented as part of a stand-alone application, as a module of an application, as a plug-in for applications including content management applications, as a library function or functions that may be called by other applications, and/or as a cloud-computing model. Thus, the components of the match determination system 100 may be implemented as part of a stand-alone application on a personal computing device or a mobile device.

Figure 9:
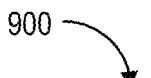
FIG. 9 illustrates an example flowchart of a series of acts for determining a source data link in accordance with one or more embodiments.
Figure 9:
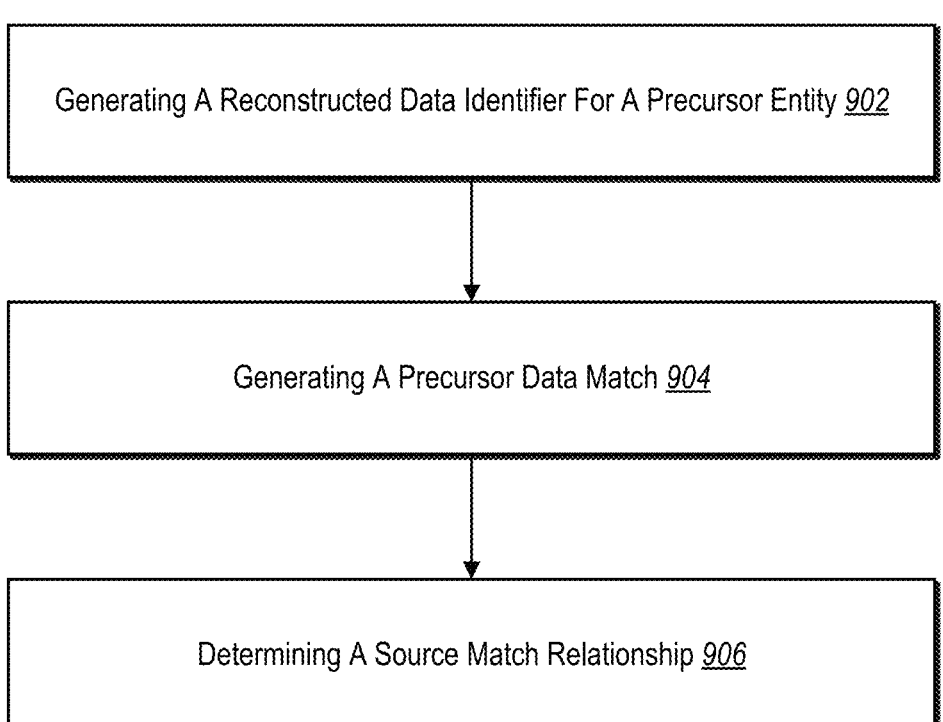

FIGS. 1-8, the corresponding text, and the examples provide a number of different systems and methods for determining a source data link in accordance with one or more embodiments. In addition to the foregoing, implementations can also be described in terms of flowcharts comprising acts steps in a method for accomplishing a particular result. For example, FIG. 9 illustrates an example flowchart of a series of acts for determining a source data link in accordance with one or more embodiments. While FIG. 9 illustrates acts according to certain implementations, alternative implementations may omit, add to, reorder, and/or modify any of the acts shown in FIG. 9. The acts of FIG. 9 can be performed as part of a method. Alternatively, a non-transitory computer-readable medium can comprise instructions, that when executed by one or more processors, cause a computing device to perform the acts of FIG. 9. In still further implementations, a system can perform the acts of FIG. 9.

As illustrated in FIG. 9, the series of acts 900 may include an act 902 of generating a reconstructed data identifier for a precursor entity. In particular, the act 902 involves generating, from a cognate dataset comprising a data identifier for a cognate related to a source individual, a reconstructed data identifier for a precursor entity corresponding to the source individual. The series of acts 900 can also include an act 904 of generating a precursor data match. In particular, the act 904 can involve generating, utilizing the reconstructed data identifier, a precursor data match between the precursor entity and a target individual. In addition, the series of acts 900 can include an act 906 of determining a source match relationship. In particular, the act 906 can involve determining a source data link between the target individual and the source individual based on the precursor data match between the precursor entity and the target individual.

In some embodiments, the series of acts 900 includes an act of generating the cognate dataset to include at least a threshold number of additional cognates related to the source individual for satisfying a threshold probability of generating the precursor data match. The series of acts 900 can also include an act of generating the reconstructed data identifier for the precursor entity by determining, for inclusion in the cognate dataset, a data identifier for the source individual and the data identifier for the cognate related to the source individual (or respective data identifiers for a plurality of individuals related to the source individual).

In one or more embodiments, the series of acts 900 includes an act of determining the source data link by: determining a precursor data link between the target individual and the precursor entity based on the precursor data match between the precursor entity and the target individual; determining a data link augmentation comprising a value augmenting the precursor data link based on a relationship between the source individual and the precursor entity; and combining the precursor data link and the data link augmentation. In at least one embodiment, the series of acts 900 includes an act of providing, in a graphical user interface of a client device, a visual indicator of the source data link between the target individual and the source individual.

Additionally, in some embodiments, the series of acts 900 includes an act of determining a data link discrepancy by: generating a source data match between the source individual and the target individual; determining an additional data link between the target individual and the source individual based on the source data match between the source individual and the target individual; and comparing the additional data link to the source data link. The series of acts 900 can also include an act of providing, in a graphical user interface of a client device, a visual indicator of the data link discrepancy and a selectable element selectable to correct the data link discrepancy using the source data link. In the same or other embodiments, the series of acts 900 can include an act of, in response to a selection of the selectable element, connecting the target individual and the source individual in a data tree based on the source data link; and providing, in the graphical user interface of the client device, a digital notification of connecting the target individual and the source individual in the data tree based on the source data link. Further, the series of acts 900 can also include an act of resolving the data link discrepancy by replacing the additional data link with the source data link determined from the precursor data match of the reconstructed data identifier.

Embodiments of the present disclosure may comprise or utilize a special purpose or general-purpose computer including computer hardware, such as, for example, one or more processors and system memory, as discussed in greater detail below. Implementations within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., a memory, etc.), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, implementations of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed by a processor, cause a general-purpose computer, special purpose computer, or special purpose processing device to perform a certain function or group of functions. In some implementations, computer-executable instructions are executed on a general-purpose computer to turn the general-purpose computer into a special purpose computer implementing elements of the disclosure. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multiprocessor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Implementations of the present disclosure can also be implemented in cloud computing environments. In this description, "cloud computing" is defined as a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

Figure 10:
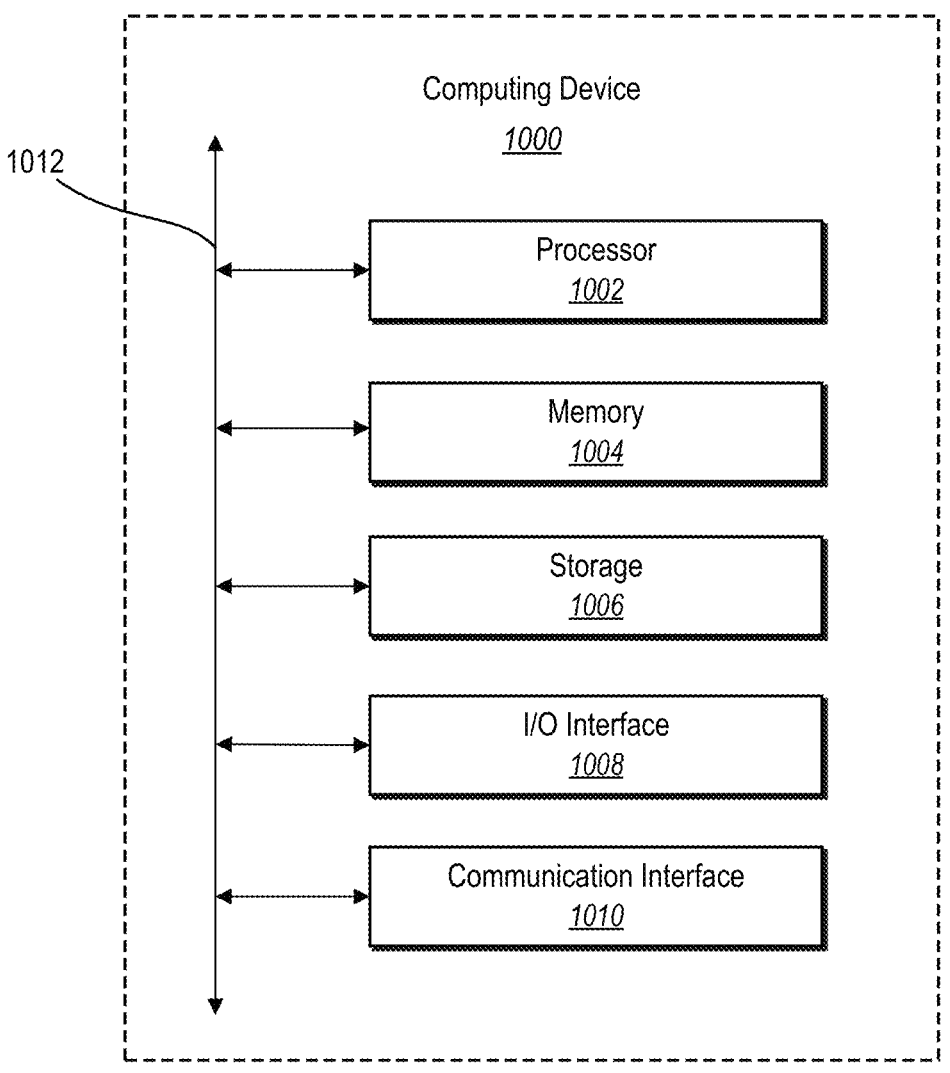
FIG. 10 illustrates a block diagram of an exemplary computing device in accordance with one or more embodiments.

FIG. 10 illustrates a block diagram of exemplary computing device 1000 (e.g., the server(s) 102, the computing server 800, and/or the client device 108) that may be configured to perform one or more of the processes described above. One will appreciate that server(s) 102 and/or the client device 108 may comprise one or more computing devices such as computing device 1000. As shown by FIG. 10, computing device 1000 can comprise processor 1002, memory 1004, storage device 1006, I/O interface 1008, and communication interface 1010, which may be communicatively coupled by way of communication infrastructure 1012. While an exemplary computing device 1000 is shown in FIG. 10, the components illustrated in FIG. 10 are not intended to be limiting. Additional or alternative components may be used in other implementations. Furthermore, in certain implementations, computing device 1000 can include fewer components than those shown in FIG. 10. Components of computing device 1000 shown in FIG. 10 will now be described in additional detail.

In particular implementations, processor 1002 includes hardware for executing instructions, such as those making up a computer program. As an example and not by way of limitation, to execute instructions, processor 1002 may retrieve (or fetch) the instructions from an internal register, an internal cache, memory 1004, or storage device 1006 and decode and execute them. In particular implementations, processor 1002 may include one or more internal caches for data, instructions, or addresses. As an example and not by way of limitation, processor 1002 may include one or more instruction caches, one or more data caches, and one or more translation lookaside buffers (TLBs). Instructions in the instruction caches may be copies of instructions in memory 1004 or storage device 1006.

Memory 1004 may be used for storing data, metadata, and programs for execution by the processor(s). Memory 1004 may include one or more of volatile and non-volatile memories, such as Random Access Memory ("RAM"), Read Only Memory ("ROM"), a solid state disk ("SSD"), Flash, Phase Change Memory ("PCM"), or other types of data storage. Memory 1004 may be internal or distributed memory.

Storage device 1006 includes storage for storing data or instructions. As an example and not by way of limitation, storage device 1006 can comprise a non-transitory storage medium described above. Storage device 1006 may include a hard disk drive (HDD), a floppy disk drive, flash memory, an optical disc, a magneto-optical disc, magnetic tape, or a Universal Serial Bus (USB) drive or a combination of two or more of these. Storage device 1006 may include removable or non-removable (or fixed) media, where appropriate. Storage device 1006 may be internal or external to comput-
ing device 1000. In particular implementations, storage
device 1006 is non-volatile, solid-state memory. In other
implementations, Storage device 1006 includes read-only
memory (ROM). Where appropriate, this ROM may be
mask programmed ROM, programmable ROM (PROM),
erasable PROM (EPROM), electrically erasable PROM
(EEPROM), electrically alterable ROM (EAROM), or flash
memory or a combination of two or more of these.

I/O interface 1008 allows a user to provide input to,
receive output from, and otherwise transfer data to and
receive data from computing device 1000. I/O interface
1008 may include a mouse, a keypad or a keyboard, a touch
screen, a camera, an optical scanner, network interface,
modem, other known I/O devices or a combination of such
I/O interfaces. I/O interface 1008 may include one or more
devices for presenting output to a user, including, but not
limited to, a graphics engine, a display (e.g., a display
screen), one or more output drivers (e.g., display drivers),
one or more audio speakers, and one or more audio drivers.
In certain implementations, I/O interface 1008 is configured
to provide graphical data to a display for presentation to a
user. The graphical data may be representative of one or
more graphical user interfaces and/or any other graphical
content as may serve a particular implementation.

Communication interface 1010 can include hardware,
software, or both. In any event, communication interface
1010 can provide one or more interfaces for communication
(such as, for example, packet-based communication)
between computing device 1000 and one or more other
computing devices or networks. As an example and not by
way of limitation, communication interface 1010 may
include a network interface controller (NIC) or network
adapter for communicating with an Ethernet or other wire-
based network or a wireless NIC (WNIC) or wireless
adapter for communicating with a wireless network, such as
a WI-FI.

Additionally or alternatively, communication interface
1010 may facilitate communications with an ad hoc net-
work, a personal area network (PAN), a local area network
(LAN), a wide area network (WAN), a metropolitan area
network (MAN), or one or more portions of the Internet or
a combination of two or more of these. One or more portions
of one or more of these networks may be wired or wireless.
As an example, communication interface 1010 may facili-
tate communications with a wireless PAN (WPAN) (such as,
for example, a BLUETOOTH WPAN), a WI-FI network, a
WI-MAX network, a cellular telephone network (such as,
for example, a Global System for Mobile Communications
(GSM) network), or other suitable wireless network or a
combination thereof.

Additionally, communication interface 1010 may facili-
tate communications various communication protocols.
Examples of communication protocols that may be used
include, but are not limited to, data transmission media,
communications devices, Transmission Control Protocol
("TCP"), Internet Protocol ("IP"), File Transfer Protocol
("FTP"), Telnet, Hypertext Transfer Protocol ("HTTP"),
Hypertext Transfer Protocol Secure ("HTTPS"), Session
Initiation Protocol ("SIP"), Simple Object Access Protocol
("SOAP"), Extensible Mark-up Language ("XML") and
variations thereof, Simple Mail Transfer Protocol
("SMTP"), Real-Time Transport Protocol ("RTP"), User
Datagram Protocol ("UDP"), Global System for Mobile
Communications ("GSM") technologies, Code Division
Multiple Access ("CDMA") technologies, Time Division
Multiple Access ("TDMA") technologies, Short Message

44

Service ("SMS"), Multimedia Message Service ("MMS"),
radio frequency ("RF") signaling technologies, Long Term
Evolution ("LTE") technologies, wireless communication
technologies, in-band and out-of-band signaling technolo-
gies, and other suitable communications networks and tech-
nologies.

Communication infrastructure 1012 may include hard-
ware, software, or both that couples components of com-
puting device 1000 to each other. As an example and not by
way of limitation, communication infrastructure 1012 may
include an Accelerated Graphics Port (AGP) or other graph-
ics bus, an Enhanced Industry Standard Architecture (EISA)
bus, a front-side bus (FSB), a HYPERTRANSPORT (HT)
interconnect, an Industry Standard Architecture (ISA) bus,
an INFINIBAND interconnect, a low-pin-count (LPC) bus,
a memory bus, a Micro Channel Architecture (MCA) bus, a
Peripheral Component Interconnect (PCI) bus, a PCI-Ex-
press (PCIe) bus, a serial advanced technology attachment
(SATA) bus, a Video Electronics Standards Association local
(VLB) bus, or another suitable bus or a combination thereof.

Figure 11:
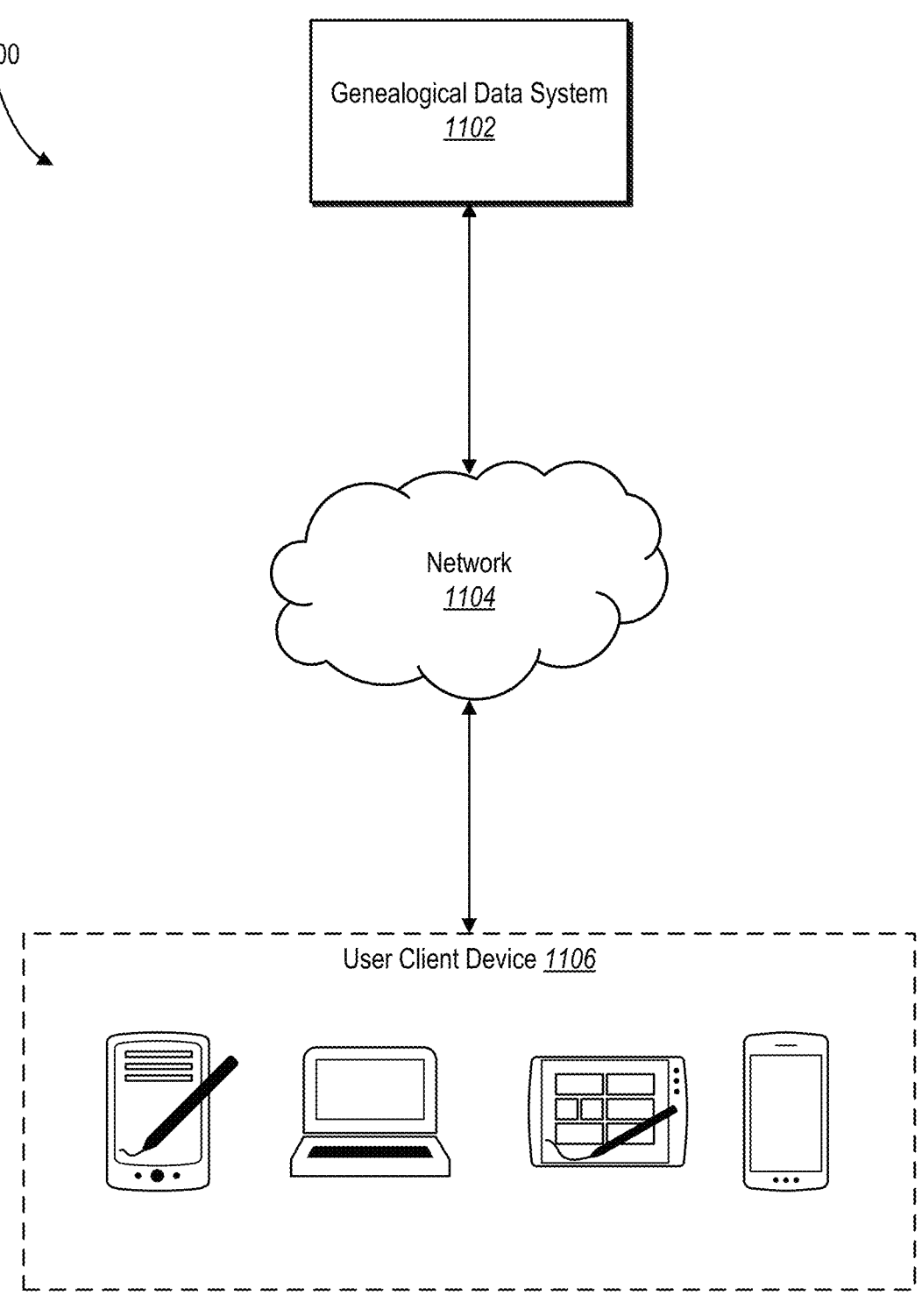
FIG. 11 illustrates an example environment of a genealogical data system including a match determination system in accordance with one or more embodiments.

FIG. 11 is a schematic diagram illustrating environment
1100 within which one or more implementations of the
match determination system 100 can be implemented. For
example, the match determination system 100 may be part
of a genealogical data system 1102 (e.g., the genealogical
data system 104). The genealogical data system 1102 may
generate, store, manage, receive, and send digital content
(such as genealogical content items). For example, genea-
logical data system 1102 may send and receive digital
content to and from client devices 1106 by way of network
1104. In particular, genealogical data system 1102 can store
and manage genealogical databases for various user
accounts, historical records, and genealogy trees. In some
embodiments, the genealogical data system 1102 can man-
age the distribution and sharing of digital content between
computing devices associated with user accounts. For
instance, the genealogical data system 1102 can facilitate a
user account sharing a genealogical content item with
another user account of genealogical data system 1102.

In particular, the genealogical data system 1102 can
manage synchronizing digital content across multiple client
devices 1106 associated with one or more user accounts. For
example, a user may edit a digitized historical document or
a node within a genealogy tree using client device 1106. The
genealogical data system 1102 can cause client device 1106
to send the edited genealogical content to the genealogical
data system 1102, whereupon the genealogical data system
1102 synchronizes the genealogical content on one or more
additional computing devices.

As shown, the client device 1106 may be a desktop
computer, a laptop computer, a tablet computer, an aug-
mented reality device, a virtual reality device, a personal
digital assistant (PDA), an in- or out-of-car navigation
system, a handheld device, a smart phone or other cellular or
mobile phone, or a mobile gaming device, other mobile
device, or other suitable computing devices. The client
device 1106 may execute one or more client applications,
such as a web browser (e.g., Microsoft Windows Internet
Explorer, Mozilla Firefox, Apple Safari, Google Chrome,
Opera, etc.) or a native or special-purpose client application
(e.g., Ancestry: Family History & DNA for iPhone or iPad,
Ancestry: Family History & DNA for Android, etc.), to
access and view content over the network 1104.

The network 1104 may represent a network or collection
of networks (such as the Internet, a corporate intranet, a
virtual private network (VPN), a local area network (LAN),
a wireless local area network (WLAN), a cellular network, a wide area network (WAN), a metropolitan area network (MAN), or a combination of two or more such networks) over which client devices 1106 may access genealogical data system 1102.

In the foregoing specification, the present disclosure has been described with reference to specific exemplary implementations thereof. Various implementations and aspects of the present disclosure(s) are described with reference to details discussed herein, and the accompanying drawings illustrate the various implementations. The description above and drawings are illustrative of the disclosure and are not to be construed as limiting the disclosure. Numerous specific details are described to provide a thorough understanding of various implementations of the present disclosure.

The present disclosure may be embodied in other specific forms without departing from its spirit or essential characteristics. The described implementations are to be considered in all respects only as illustrative and not restrictive. For example, the methods described herein may be performed with less or more steps/acts or the steps/acts may be performed in differing orders. Additionally, the steps/acts described herein may be repeated or performed in parallel with one another or in parallel with different instances of the same or similar steps/acts. The scope of the present application is, therefore, indicated by the appended claims rather than by the foregoing description. All changes that come within the meaning and range of equivalency of the claims are to be embraced within their scope.

What is claimed is:

1. A computer-implemented method comprising:
generating, from a cognate dataset comprising a data identifier for a cognate related to a source individual, a reconstructed data identifier for a precursor entity corresponding to the source individual;
generating, utilizing the reconstructed data identifier, a precursor data match between the precursor entity and a target individual;
determining a precursor data link between the target individual and the precursor entity based on the precursor data match between the precursor entity and the target individual;
determining a data link augmentation comprising a value augmenting the precursor data link based on a relationship between the source individual and the precursor entity; and
determining a source data link between the target individual and the source individual by combining the precursor data link and the data link augmentation.

2. The computer-implemented method of claim 1, wherein generating the reconstructed data identifier for the precursor entity comprises determining, for inclusion in the cognate dataset, a data identifier for the source individual and the data identifier for the cognate related to the source individual.

3. The computer-implemented method of claim 2, wherein generating the reconstructed data identifier for the precursor entity further comprises:
identifying one or more phased data segments inherited from the precursor entity by comparing the data identifier for the cognate related to the source individual and the data identifier for the source individual included in the cognate dataset;
generating a set of cognate phased data segments by extracting the one or more phased data segments; and
determining data exchange breakpoints in the set of cognate phased data segments.

4. The computer-implemented method of claim 1, further comprising determining a data link discrepancy by:
generating a source data match between the source individual and the target individual;
determining an additional data link between the target individual and the source individual based on the source data match between the source individual and the target individual; and
comparing the additional data link to the source data link.

5. The computer-implemented method of claim 4, further comprising providing, in a graphical user interface of a client device, a visual indicator of the data link discrepancy and a selectable element selectable to correct the data link discrepancy using the source data link.

6. The computer-implemented method of claim 5, further comprising:
in response to a selection of the selectable element, connecting the target individual and the source individual in a data tree based on the source data link; and
providing, in the graphical user interface of the client device, a digital notification of connecting the target individual and the source individual in the data tree based on the source data link.

7. The computer-implemented method of claim 4, further comprising resolving the data link discrepancy by replacing the additional data link with the source data link determined using the precursor data match between the precursor entity and the target individual.

8. A system comprising:
at least one processor; and
at least one non-transitory computer-readable storage medium storing instructions that, when executed by the at least one processor, cause the system to:
generate, from a cognate dataset comprising respective data identifiers for a plurality of cognates related to a source individual, a reconstructed data identifier for a precursor entity corresponding to the source individual;
generate, utilizing the reconstructed data identifier, a precursor data match between the precursor entity and a target individual;
determine a precursor data link between the target individual and the precursor entity based on the precursor data match between the precursor entity and the target individual;
determine a data link augmentation comprising a value augmenting the precursor data link based on a relationship between the source individual and the precursor entity; and
determine a source data link between the target individual and the source individual by combining the precursor data link and the data link augmentation.

9. The system of claim 8, further comprising instructions that, when executed by the at least one processor, cause the system to generate the reconstructed data identifier for the precursor entity by determining, for inclusion in the cognate dataset, a data identifier for the source individual and the respective data identifiers for the plurality of cognates related to the source individual.

10. The system of claim 8, further comprising instructions that, when executed by the at least one processor, cause the system to generate the reconstructed data identifier for the precursor entity by:
identifying one or more phased data segments inherited from the precursor entity by comparing the respective data identifiers for the plurality of cognates related to the source individual and a data identifier for the source individual included in the cognate dataset;

generating a set of cognate phased data segments by extracting the one or more phased data segments; and determining data exchange breakpoints in the set of cognate phased data segments.

11. The system of claim 8, further comprising instructions that, when executed by the at least one processor, cause the system to determine a data link discrepancy by:

generating a source data match between the source individual and the target individual;

determining an additional data link between the target individual and the source individual based on the source data match between the source individual and the target individual; and comparing the additional data link to the source data link.

12. The system of claim 11, further comprising instructions that, when executed by the at least one processor, cause the system to provide, in a graphical user interface of a client device, a visual indicator of the data link discrepancy and one or more selectable elements selectable to correct the data link discrepancy using the source data link.

13. The system of claim 12, further comprising instructions that, when executed by the at least one processor, cause the system to:

in response to a selection of the one or more selectable elements, connect the target individual and the source individual in a data tree based on the source data link; and provide, in a graphical user interface of a client device, a digital notification of connecting the target individual and the source individual in the data tree based on the source data link.

14. The system of claim 11, further comprising instructions that, when executed by the at least one processor, cause the system to resolve the data link discrepancy by replacing the additional data link with the source data link determined using the precursor data match between the precursor entity and a target individual.

15. A computer-implemented method comprising:

generating, from a cognate dataset comprising a data identifier for a cognate related to a source individual, a reconstructed data identifier for a precursor entity corresponding to the source individual;

generating, utilizing the reconstructed data identifier, a precursor data match between the precursor entity and a target individual;

determining a source data link between the target individual and the source individual based on the precursor data match between the precursor entity and the target individual; and determining a data link discrepancy by:

generating a source data match between the source individual and the target individual;

determining an additional data link between the target individual and the source individual based on the source data match between the source individual and the target individual; and comparing the additional data link to the source data link.

16. The computer-implemented method of claim 15, further comprising resolving the data link discrepancy by replacing the additional data link with the source data link determined using the precursor data match between the precursor entity and the target individual.

17. The computer-implemented method of claim 15, wherein determining the source data link comprises:

determining a precursor data link between the target individual and the precursor entity based on the precursor data match between the precursor entity and the target individual;

determining a data link augmentation comprising a value augmenting the precursor data link based on a relationship between the source individual and the precursor entity; and combining the precursor data link and the data link augmentation.

18. The computer-implemented method of claim 15, wherein generating the reconstructed data identifier for the precursor entity further comprises:

identifying one or more phased data segments inherited from the precursor entity by comparing the data identifier for the cognate related to the source individual and the data identifier for the source individual included in the cognate dataset;

generating a set of cognate phased data segments by extracting the one or more phased data segments; and determining data exchange breakpoints in the set of cognate phased data segments.

19. The computer-implemented method of claim 15, further comprising providing, in a graphical user interface of a client device, a visual indicator of the data link discrepancy and one or more selectable elements selectable to correct the data link discrepancy using the source data link.

20. The computer-implemented method of claim 19, further comprising:

in response to a selection of the one or more selectable elements, connecting the target individual and the source individual in a data tree based on the source data link; and providing, in a graphical user interface of a client device, a digital notification of connecting of the target individual and the source individual in the data tree based on the source data link.

* * * * *